(12) United States Patent
Maki et al.

(10) Patent No.: US 6,695,871 B1
(45) Date of Patent: *Feb. 24, 2004

(54) THERMAL THERAPY APPARATUS

(75) Inventors: Shin Maki, Nakai-machi (JP); Akira Sakaguchi, Nakai-machi (JP); Shigeki Ariura, Nakai-machi (JP)

(73) Assignee: Terumo Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/637,331

(22) Filed: Aug. 10, 2000

(30) Foreign Application Priority Data

| Aug. 13, 1999 | (JP) | 11-229476 |
| Aug. 13, 1999 | (JP) | 11-229478 |
| Aug. 13, 1999 | (JP) | 11-229480 |

(51) Int. Cl.[7] ............................................. A61N 5/06
(52) U.S. Cl. ................................... 607/89; 606/10
(58) Field of Search .................. 606/2, 7, 8, 10–16

(56) References Cited

U.S. PATENT DOCUMENTS

| 4,211,229 A | 7/1980 | Wurster |
| 4,620,546 A | 11/1986 | Itoh et al. |
| 4,638,436 A | 1/1987 | Burdette et al. |
| 4,672,963 A * | 6/1987 | Barken .................. 606/12 |
| 4,932,956 A | 6/1990 | Reddy et al. |
| 4,932,958 A | 6/1990 | Reddy et al. |
| 5,049,147 A * | 9/1991 | Danon .................. 606/10 |
| 5,050,597 A | 9/1991 | Daikuzono |
| 5,207,672 A | 5/1993 | Roth et al. |
| 5,248,311 A | 9/1993 | Black et al. |
| 5,292,320 A | 3/1994 | Brown et al. |
| 5,350,375 A | 9/1994 | Deckelbaum et al. |
| 5,377,683 A | 1/1995 | Barken |
| 5,450,846 A | 9/1995 | Goldreyer |
| 5,496,308 A | 3/1996 | Brown et al. |
| 5,769,843 A | 6/1998 | Abela et al. |
| 6,171,303 B1 | 1/2001 | Ben-Haim et al. |
| 6,321,109 B2 | 11/2001 | Ben-Haim et al. |
| 2001/0053907 A1 | 12/2001 | Ota |

FOREIGN PATENT DOCUMENTS

| EP | 0 673 627 A1 | 9/1995 |
| JP | 2001-46389 | 2/2001 |
| WO | WO 92/04934 | 4/1992 |
| WO | WO 03/04727 | 3/1993 |
| WO | WO 93/04727 * | 3/1993 .......... A61M/25/10 |

* cited by examiner

Primary Examiner—Roy D. Gibson
Assistant Examiner—Pete Vrettakos
(74) Attorney, Agent, or Firm—Burns, Doane, Swecker & Mathis, LLP

(57) ABSTRACT

In a thermal therapy apparatus for treating a vital tissue by irradiating the tissue with a laser beam, a display unit displays a figure indicating the shape of a diseased part to be heated on the basis of information concerning the diseased part. Heating regions are arranged in the displayed figure indicating the diseased part shape by using identifiers corresponding to individual heating conditions. In accordance with size/position information of these heating regions arranged, heating conditions such as the laser intensity laser irradiation time and laser irradiation angle are set. Laser beam irradiation is performed by controlling the irradiation in accordance with the set heating conditions. The information pertaining to the diseased part can also be input on the basis of an ultrasonic signal from an ultrasonic probe separated from or installed in the laser irradiation portion.

44 Claims, 31 Drawing Sheets

FIG. 10

| SET ITEM | UNIT | TEMPLATES | | |
|---|---|---|---|---|
| | | A | B | C |
| LASER POWER | W | 8 | 10 | 12 |
| IRRADIATION TIME | sec | 120 | 180 | 240 |
| COOLANT FLOW RATE | ml / min | 150 | 200 | 250 |
| DRIVING VELOCITY | ROUND TRIPS / sec | 2 | 3 | 4 |

| TEMPLATES 102 W | °C | ml/min | TIME |
|---|---|---|---|
|  |  |  |  |

FIG. 22

| SET ITEM | UNIT | THERAPEUTIC CONDITION SELECTION | |
|---|---|---|---|
| | | A | B |
| LASER POWER | W | 8 | 12 |
| IRRADIATION TIME | sec | 120 | 240 |
| COOLANT FLOW RATE | ml / min | 150 | 250 |
| DRIVING VELOCITY | ROUND TRIPS/ sec | 2 | 4 |

FIG. 33

| SET ITEM | UNIT | THERAPEUTIC CONDITIONS | | |
|---|---|---|---|---|
| | | MINIMUM | B | MAXIMUM |
| LASER POWER | W | 8 | 10 | 12 |
| IRRADIATION TIME | sec | 120 | 180 | 240 |
| COOLANT FLOW RATE | ml / min | 150 | 200 | 250 |
| DRIVING VELOCITY | ROUND TRIPS/ sec | 2 | 3 | 4 |

THERMAL THERAPY APPARATUS

FIELD OF THE INVENTION

The present invention relates to a thermal therapy apparatus which is placed by insertion or centesis in a body cavity or tract such as a blood vessel, digestive tract, urinary tract, abdominal cavity, or thoracic cavity, a nd performs thermal therapy by energy irradiation by using, e.g., a laser beam, microwave, radio frequency, or ultrasonic wave.

BACKGROUND OF THE INVENTION

A thermal therapy apparatus is known which uses a long insertion portion to be inserted into a human body by using a body cavity or performing small incision on the human body. This insertion portion irradiates a lesion portion of the human body with, e.g., a laser beam to extinguish a tissue of this morbid by heating, degeneration, necrosis, coagulation, cauterization, or vaporization, thereby heating and treating the lesion portion. Generally, this thermal therapy apparatus irradiates a lesion portion in a surface layer or its vicinity of a vital tissue directly with a laser beam.

Another technique is also known which irradiates a deep portion of avital tissue with energy to treat a lesion portion positioned deep inavital tissue, i.e., to treat a deep lesion portion, such as in thermal therapy of a prostate. International Patent Laid-Open No. 6-510450 has disclosed a technique to provide a method of coagulating and reducing a partial tissue of a tumor or prostate by laser irradiation. This technique does not heat the surface of a urethra in contact with a balloon by injecting a coolant into the balloon, but heats only an internal prostate.

Thermal therapy apparatuses described above are classified into apparatuses whose therapeutic conditions are fixed and unchangeable and apparatuses whose therapeutic conditions can be appropriately set. Regardless of the type of thermal therapy apparatus for performing thermal therapy, the general approach is to perform image diagnosis on a tissue containing a lesion portion to be thermally treated or on peripheral tissues of the lesion portion, prior to determining whether the thermal therapy is to be performed. That is, the shape of a tissue containing a lesion portion to be thermally treated, the positional relationship with peripheral tissues, the shape of the lesion portion, and the seriousness of the lesion portion are diagnosed. These diagnoses are done by using a separate image diagnosis dedicated apparatus not included in a thermal therapy apparatus or a thermal therapy apparatus capable of performing both image diagnoses using an endoscope or an ultrasonic wave and thermal therapy.

On the basis of the results of such image diagnoses in addition to the experience of an operator, therapeutic conditions such as the intensity (output) of energy, e.g., a laser beam, microwave, radio frequency, or ultra sonic wave, the irradiation time, the irradiation direction, the irradiation position, the number of times of irradiation, the coolant temperature when a coolant is used, and the coolant flow rate when the coolant is circulated are individually set.

The heating conditions of such a thermal therapy apparatus are set on the basis of the knowledge and experience of an operator. Hence, it is difficult to know what size of a heating range is obtained by setting the individual therapeutic conditions to what degrees. This means that the larger the number of set items of therapeutic conditions, the more difficult it becomes to know the heating range obtained. Therefore, wrong therapeutic conditions may be set if an operator determines the therapeutic conditions. If wrong therapeutic conditions are set, the heating energy may become excessive or the heating position may deviate to give damage to normal tissues around a lesion portion. Alternatively, the heating energy may become too insufficient to obtain a satisfactory therapeutic effect.

Also, in a medical heating apparatus for performing thermal therapy on a human body by using a laser beam or the like, the irradiation direction and position of the laser beam and the number of times of irradiation are set on the basis of the knowledge, experience, and skill of an operator. This may lead to duplicate the heating portion or heat the non-heating portion.

Furthermore, in a conventional thermal therapy apparatus, an operator must understand image diagnostic information, set therapeutic conditions, and input the set conditions to the thermal therapy apparatus. Since this input work is cumbersome, not only the time necessary for preparations of thermal therapy increases, but also wrong therapeutic conditions may be set. Consequently, the heating energy may become excessive to give damage to normal tissues around a lesion portion or may become too insufficient to obtain a satisfactory therapeutic effect.

Moreover, diverse diagnostic data of individual patients are rarely mistaken to set wrong therapeutic conditions.

SUMMARY OF THE INVENTION

The present invention has been made in consideration of the above prior art, and has as its object to provide a thermal therapy apparatus capable of performing energy irradiation by easily setting a region to be heated by the energy irradiation on the basis of the shape of a diseased part.

It is another object of the present invention to provide a thermal therapy apparatus capable of performing thermal therapy by automatically setting thermal therapeutic conditions of a diseased part on the basis of shape data of the diseased part and performing energy irradiation by controlling the irradiation angle of the energy, the number of times of irradiation, and the like in accordance with the set thermal therapeutic conditions.

It is still another object of the present invention to provide a thermal therapy apparatus capable of performing thermal therapy by energy irradiation by easily setting a heating region by fitting an identifier corresponding to a heating range and heating conditions into a displayed sectional shape.

It is still another object of the present invention to provide a medical heating apparatus capable of reducing the load on an operator required for preparations of thermal therapy and setting therapeutic conditions corresponding to the shape of a diseased part of a patient.

It is still another object of the present invention to provide a medical heating apparatus capable of directly acquiring information concerning the shape of a vital tissue to be thermally treated and performing the thermal therapy by automatically setting therapeutic conditions matching the acquired information.

To achieve the above objects, a thermal therapy apparatus of the present invention has the following arrangement.

A thermal therapy apparatus for treating a vital tissue by irradiating the tissue with energy, comprises display means for displaying a figure indicating the shape of a diseased part to be heated on the basis of information concerning the diseased part, operating means for arranging a heating region in the figure indicating the diseased part shape displayed on the display means, and control means for controlling therapeutic conditions of the thermal therapy apparatus in accordance with size/position information of the heating region arranged by the operating means.

Also, a thermal therapy apparatus of the present invention has the following arrangement.

A thermal therapy apparatus comprises energy irradiation means to be inserted into a human body to irradiate a diseased part with energy, approximating means for approximating the shape of the diseased part on the basis of shape data of the diseased part, setting means for setting a non-heating region in the shape approximated by the approximating means, allocating means for allocating heating regions, to be heated by the energy from the energy irradiation means, in a target heating region except for the non-heating region set by the setting means, such that the heating regions are substantially uniformly arranged, and display means for displaying a figure indicating the diseased part shape approximated by the approximating means, the heating regions allocated by the allocating means, and the non-heating region set by the setting means.

Desirably, a plurality of identifiers corresponding to thermal therapeutic conditions of the thermal therapy apparatus are stored, and the allocating means selects an optimum identifier from the plurality of identifiers, and arranges the heating region by arranging the selected identifier in the figure.

The thermal therapy apparatus desirably further comprises setting means for setting a non-heating region in the figure indicating the diseased part shape.

The irradiation angle and the number of times of irradiation of the energy are desirably determined in accordance with the arrangement of the heating region.

Furthermore, a thermal therapy apparatus of the present invention has the following arrangement.

A medical heating apparatus for performing thermal therapy by irradiating a vital tissue with energy, comprises image acquiring means for acquiring an image signal of a diseased part as an object of the thermal therapy, signal analyzing means for analyzing the image signal acquired by the image acquiring means, setting means for setting therapeutic conditions for performing the thermal therapy on the basis of analytical information obtained by the signal analyzing means, and irradiation means for irradiating the diseased part with energy.

In the present invention, the therapeutic conditions preferably include at least the energy output intensity and the irradiation time.

Desirably, the energy is transmitted in a catheter and concentrated on a desired portion in a human body while the position is changed in the catheter.

The energy is preferably a laser beam.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 10 is a view showing irradiation conditions corresponding to different pallets;

FIG. 22 is a view for explaining laser irradiation conditions according to the third embodiment of the present invention;

FIG. 33 is a view for explaining therapeutic conditions according to this embodiment.

DETAILED DESCRIPTION OF THE PREFERRED EMBODIMENTS

Preferred embodiments of the present invention will be described below with reference to the accompanying drawings.

Figure 1:
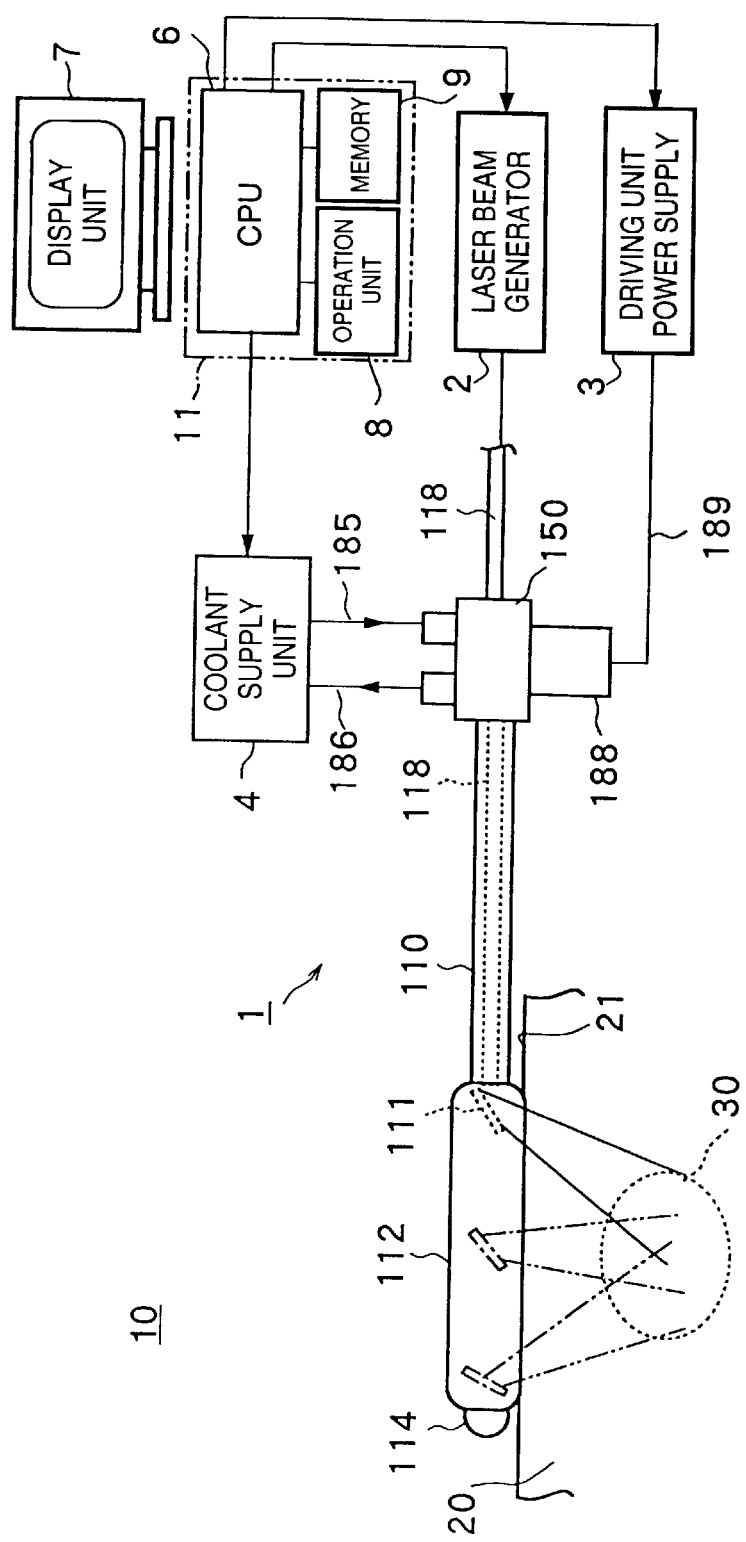
FIG. 1 is a block diagram showing the arrangement of a medical laser irradiation apparatus (thermal therapy apparatus) of this embodiment.

FIG. 1 is a block diagram showing the arrangement of a medical laser irradiation apparatus 10 as one example of a thermal therapy apparatus according to this embodiment.

Referring to FIG. 1, this medical laser irradiation apparatus 10 has a side-emission-type laser irradiation catheter 1 for irradiating a vital tissue with a laser beam. That is, a main body 110 as a long insertion portion of the laser irradiation catheter 1 of this medical laser irradiation apparatus 10 is inserted into a human body. A reflecting portion 111 contained in this main body 110 reflects the laser beam to irradiate a vital tissue 20. For example, this medical laser irradiation apparatus 10 is used to treat BPH: benign prostatic hyperplasia or to heat or cauterize or cut tumors such as various cancers.

Figure 2:
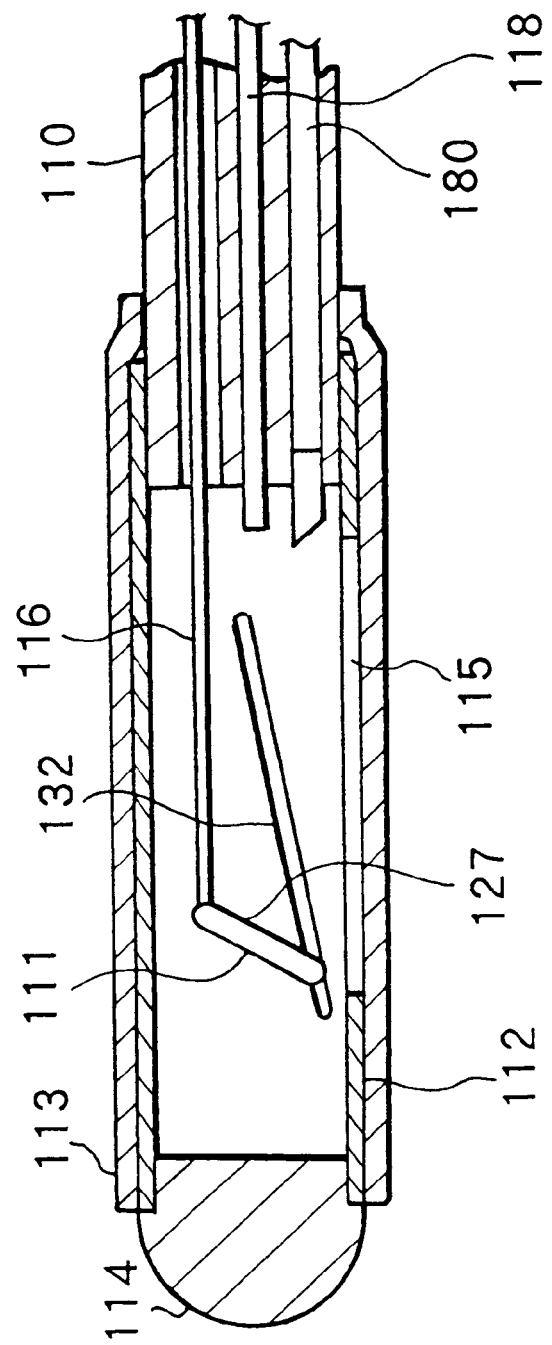
FIG. 2 is a sectional view for explaining the structure of a housing.
Figure 3:
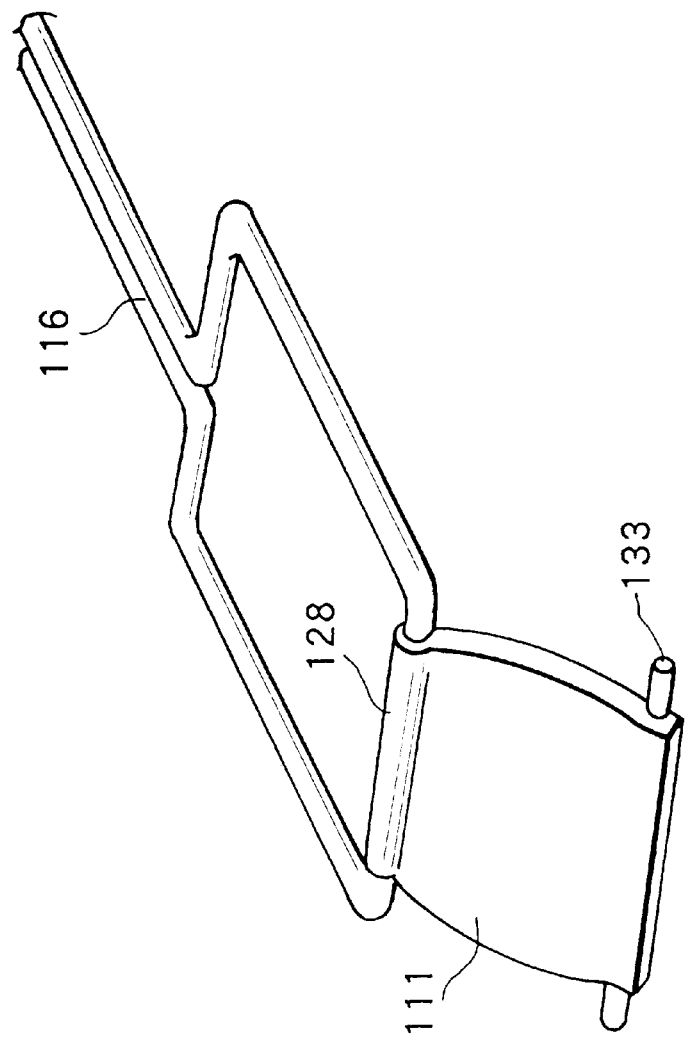
FIG. 3 is a view for explaining an arm for displacing a reflecting portion and the reflecting portion.

FIG. 2 is a sectional view of a housing 112 of the laser irradiation catheter. FIG. 3 is a view for explaining the shapes of an arm 116 and the reflecting portion 111.

In FIGS. 1 to 3, the laser irradiation catheter 1 includes the long main body 110, the reflecting portion 111 for reflecting a laser beam, output by a laser beam generator 2 and propagating in an optical fiber 118, and performing irradiation of this laser beam into the human body 20, and the housing 112 containing the reflecting portion 111 and connected to the end portion of the main body 110. The arm 116 is connected to the reflecting portion 111 to support this reflecting portion 111 in the housing 112. By moving this arm 116 in the axial direction of the main body 110, the reflecting portion 111 is moved in the axial direction. This reflecting portion 111 has a smooth reflecting surface 127 formed on one surface of the reflecting portion 111 to reflect a laser beam propagating in the optical fiber 118.

The housing 112 is a hard tubular member having a window 115 for laser beam irradiation and is covered with a cover member 113 which transmits a laser beam. To change the irradiation angle of the reflecting portion 111, this housing 112 has inner walls in which a pair of grooves 132 are formed which engage with projections 133 (FIG. 3) formed on the two sides of the reflecting portion 111. The grooves 132 thus functioning as guides for the reflecting portion 111 are formed on the two sides of the inner walls with the reflecting portion 111 being sandwiched between them. These grooves 132 are non-parallel to the axial direction of the main body 110, i.e., inclined to the axial direction of the main body 110. The distal end portion of the housing 112 is sealed with a cap 114.

The optical fiber 118 as a light guiding means for guiding abaser beam is placed inside the main body 110. This optical fiber 118 functions as an energy transmitting member. Note that a lens can also be formed at the tip of this optical fiber 118. When this is the case, this tip lens is an optical element for collimating a laser beam. The optical fiber 118 transmits a laser beam generated by the laser beam generator 2.

The laser irradiation catheter 1 further has a detachable, obliquely viewing type endoscope 180 (FIG. 2). This endoscope 180 is inserted from the proximal end portion to the distal end portion of the laser irradiation catheter 1. An optical fiber of the endoscope 180 for illuminating light irradiation also has a function of guide light irradiation. Accordingly, it is possible to observe a surface layer to be irradiated with a laser beam, position the housing 112 based on the endoscopic observation, and visually confirm the irradiation position of a laser beam.

FIG. 3 is a perspective view for explaining the structures of the reflecting portion 111 and the arm 116 of the laser irradiation catheter 1.

The arm 116 supports the reflecting portion 111 by branching into left- and right-hand portions in the housing 112. Hence, this arm 116 does not prevent the surface of the reflecting portion 111 from being irradiated with a laser beam. A support portion 128 is formed on one edge of the reflecting portion 111, and the pair of projections 133 are formed on the other edge. The support portion 128 is attached to the arm 116 so as to be freely rotatable. Therefore, this support portion 128 can rotate in accordance with changes in the irradiation angle of the reflecting portion 111.

The arm 116 is connected to a driving unit 150 placed in the proximal end portion of the laser irradiation catheter 1. Note that this driving unit 150 can also be placed outside the laser irradiation catheter 1 to connect the arm 116 to the driving unit 150 via a drive shaft. As this drive shaft, a metal wire or the like can be used.

The driving unit 150 is connected to a motor 188 to which electric power is supplied from a driving unit power supply 3 via a cable 189. On the basis of a control signal from a CPU 6, the driving unit power supply 3 supplies electric power at a predetermined voltage or current to the motor 188 and thereby rotate the motor 188. Examples of the motor 188 are an induction motor, servo motor, and stepping motor.

The driving unit 150 moves the reflecting portion 111 back and forth in the axial direction of the main body 110. The driving unit power supply 3, the motor 188, and the driving unit 150 constitute a moving means for moving the reflecting portion 111 in the axial direction of the main body 110. On the basis of the cooperation of the arm 116 and the grooves 132, the reflecting portion 111 changes its inclination angle in accordance with the position in the axial direction.

Figure 4:
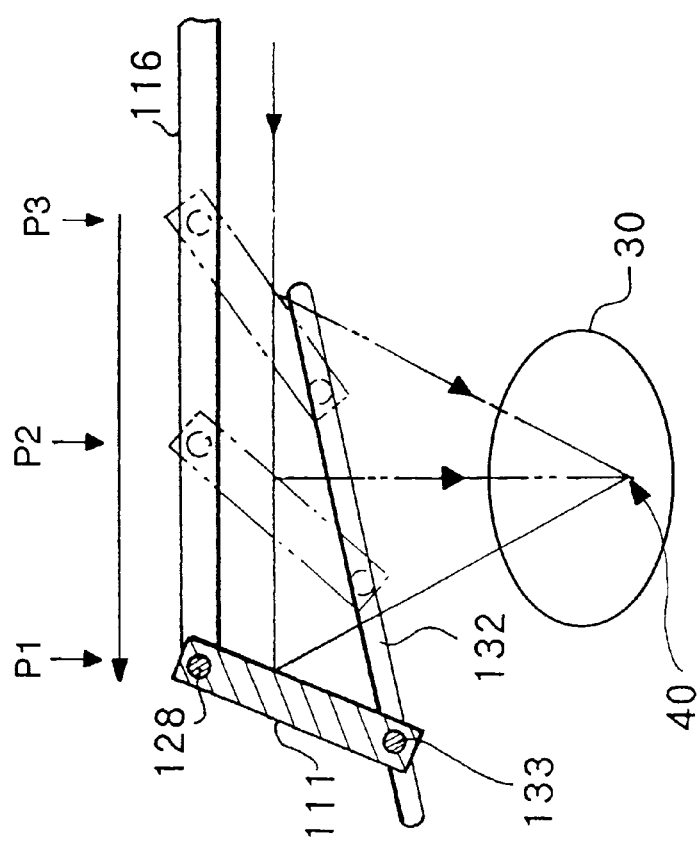
FIG. 4 is a view for explaining displacement of the reflecting portion.

FIG. 4 is a view for explaining the relationship between the movement of the reflecting portion 111 and the laser beam irradiation direction.

As shown in FIG. 4, the distance between the arm 116 and the grooves 132 not parallel to the arm 116 in a position P2 is shorter than that in a position P1. Accordingly, when the support portion 128 of the reflecting portion 111 moves from the position P1 to the position P2, the projections 133 of the reflecting portion 127 slide along the grooves 132 to adjust the inclination angle of the reflecting portion 111. That is, the inclination angle of the reflecting portion 111 with respect to the axis of the main body 110 decreases. Likewise, when the support portion 128 of the reflecting portion 111 moves from the position P2 to a position P3, the inclination angle of the reflecting portion 111 with respect to the axis of the main body 110 further decreases. Meanwhile, in these positions P1 to P3 the laser beam reflected by the reflecting portion 111 concentrates on a target point 40 in a target portion 30 which is a lesion portion, i.e., a portion to be heated.

That is, only the target point 40 is continuously irradiated with the laser beam, and other tissues such as the surface layer are intermittently irradiated. Therefore, the target point 40 is heated by the laser beam to reach a desired temperature. On the other hand, other tissues such as the surface layer are hardly heated because the laser beam irradiation time per predetermined area is short and hence the amount of generated heat is small. Note that the laser irradiation catheter 1 is applicable to lesion portions having complicated shapes by properly designing the relationship between the arm 116 parallel to the axial direction of the main body 110 and the grooves 132 not parallel to the axial direction, or the shape of the grooves 132. For example, the grooves 132 need not be straight grooves but can be curved grooves.

Referring back to FIG. 1, a coolant supply unit 4 circulates, in the main body 110, a coolant for suppressing the generation of heat in the housing 112 by a laser beam via an injection tube 185 and a discharge tube 186. A display unit 7 is a CRT or a liquid crystal display. A controller 11 includes the CPU 6 such as a microprocessor, a memory 9 storing programs to be executed by the CPU 6 and various data, and an operation unit 8 including, e.g., a keyboard, a pointing device, and diverse switches.

Figure 5:
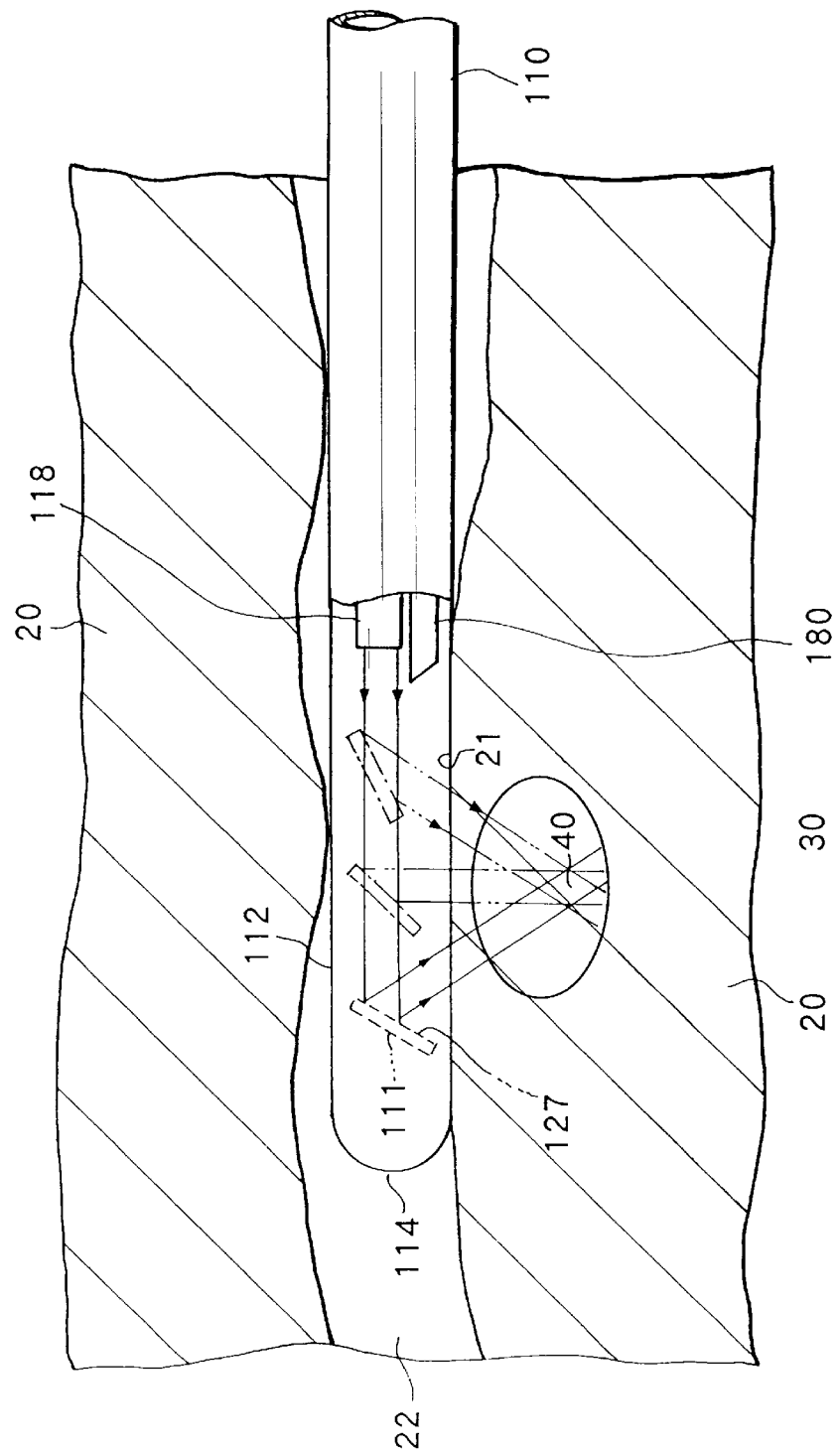
FIG. 5 is a view for explaining an example use of a laser irradiation catheter of this embodiment.

FIG. 5 is a sectional view for explaining an application of the laser irradiation catheter 1. The distal end portion of the main body 110 is inserted into a body cavity 22 of a human body. The housing 112 which accommodates the reflecting portion 111 is brought into tight contact with a surface layer 21 near the target portion 30 as a lesion portion, i.e., a portion to be heated. It is desirable to directly confirm the position of the housing 112 by the endoscope 180. Note that the position of the target point 40 in the longitudinal direction of the main body 110 is adjusted by moving the whole laser irradiation catheter 1 in the longitudinal direction of the main body 110. Also, the position of the target point 40 in the circumferential direction of the main body 110 can be adjusted by manually or automatically rotating the entire laser irradiation catheter 1. During laser beam irradiation, the reflecting portion 111 is moved back and forth in the axial direction, while its angle is changed at a period of 0.1 to 10 Hz, preferably 1 to 6 Hz. Although the optical path of the laser beam is thus continuously changed, the laser beam so irradiates that all optical paths cross each other at the target point 40. Consequently, the target point 40 and its vicinity are heated by the irradiated laser beam to reach a predetermined temperature. In this manner, only the temperature in the desired portion 30 can be raised while a temperature rise in the surface layer 21 is suppressed.

Note that the laser beam is preferably divergent light, parallel light, or convergent light. An optical system which collimates a laser beam into convergent light can also be placed midway along the optical path of the laser beam. The laser beam used is not particularly limited as long as the beam is capable of reaching a deep part in a human body.

The wavelength is preferably 750 to 1,300 nm, or 1,600 to 1,800 nm. For example, a gas laser such as an He-Ne laser, a solid laser such as an Nd-YAG laser, and a semiconductor laser such as a GaAlAs laser can be applied to the laser beam generator 2 for generating a laser beam having the above wavelength.

Also, the diameter of the insertion portion of the laser irradiation catheter 1, i.e., the outer diameter of the main body 110 is not particularly restricted, provided that the diameter allows insertion into the body cavity 22. However, the outer diameter of the main body 110 is preferably about 2 to 20 mm, and more preferably, 3 to 8 mm.

First Embodiment

The characteristic features of a medical laser irradiation apparatus 10 according to the first embodiment will be described below. This medical laser irradiation apparatus 10 is a laser irradiation apparatus by which a main body 110 is inserted into a urethra to irradiate a prostate around the urethra with a laser beam, thereby treating BPH: benign prostatic hyperplasia.

Figure 6:
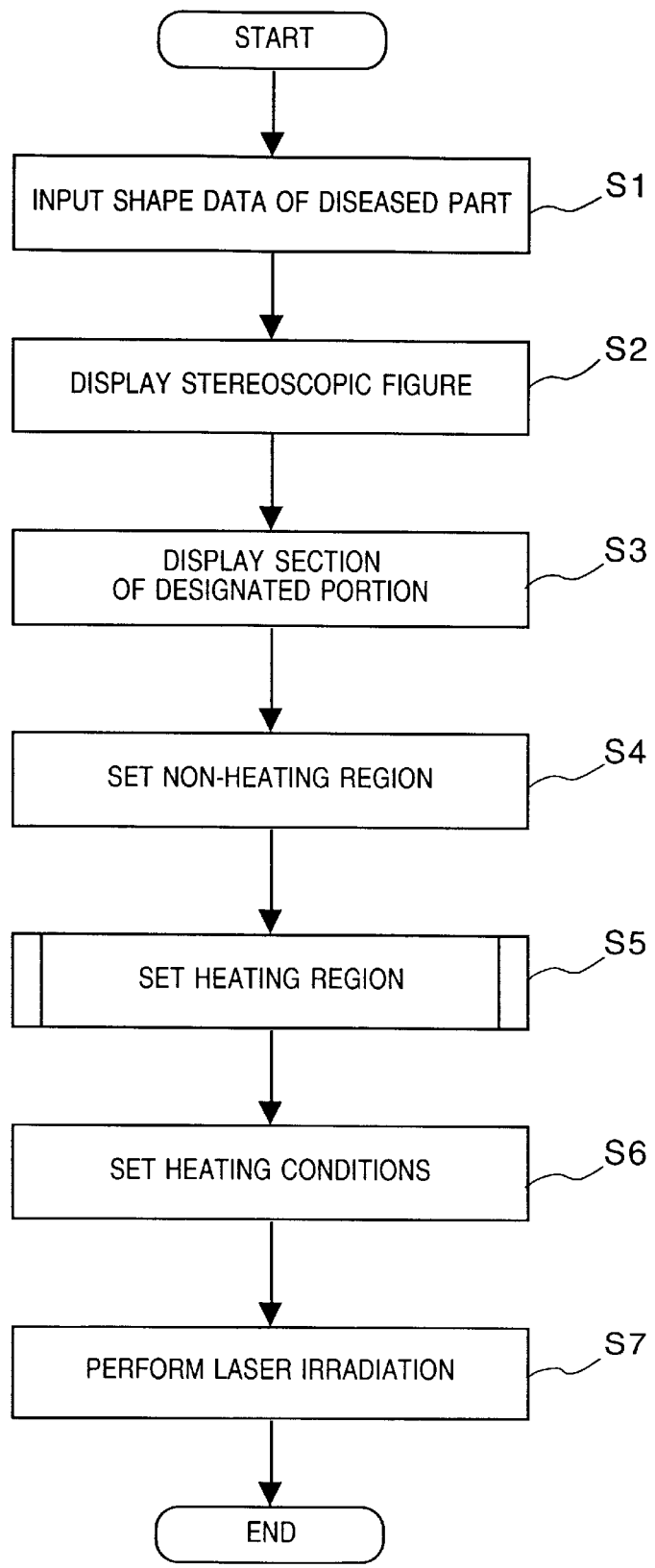
FIG. 6 is a flow chart showing a laser irradiation process by a medical laser irradiation apparatus of the first embodiment of the present invention.

FIG. 6 is a flow chart showing a laser beam irradiation control process by the medical laser irradiation apparatus of this embodiment. A control program for executing this process is stored in a memory 9 of a controller 11 and executed under the control of a CPU 6.

In step S1, the position and size of a diseased part to be treated are input from an operation unit 8. That is, on the basis of diagnostic data such as transurethral ultrasonic diagnosis, transabdominal ultrasonic diagnosis, transrectal ultrasonic diagnosis, MRI, and X-ray CT, three-dimensional lengths x, y, and z of the diseased part are measured, and an operator manually inputs the measurement results from the operation unit 8. It is also possible to directly input an image sensed by the ultrasonic diagnostic apparatus and automatically measure and input the position and size of the diseased part. When the position/size information of the diseased part is thus input, the flow advances to step S2 to display a three-dimensional image of the diseased part on the basis of the input position/size information.

Figure 8:
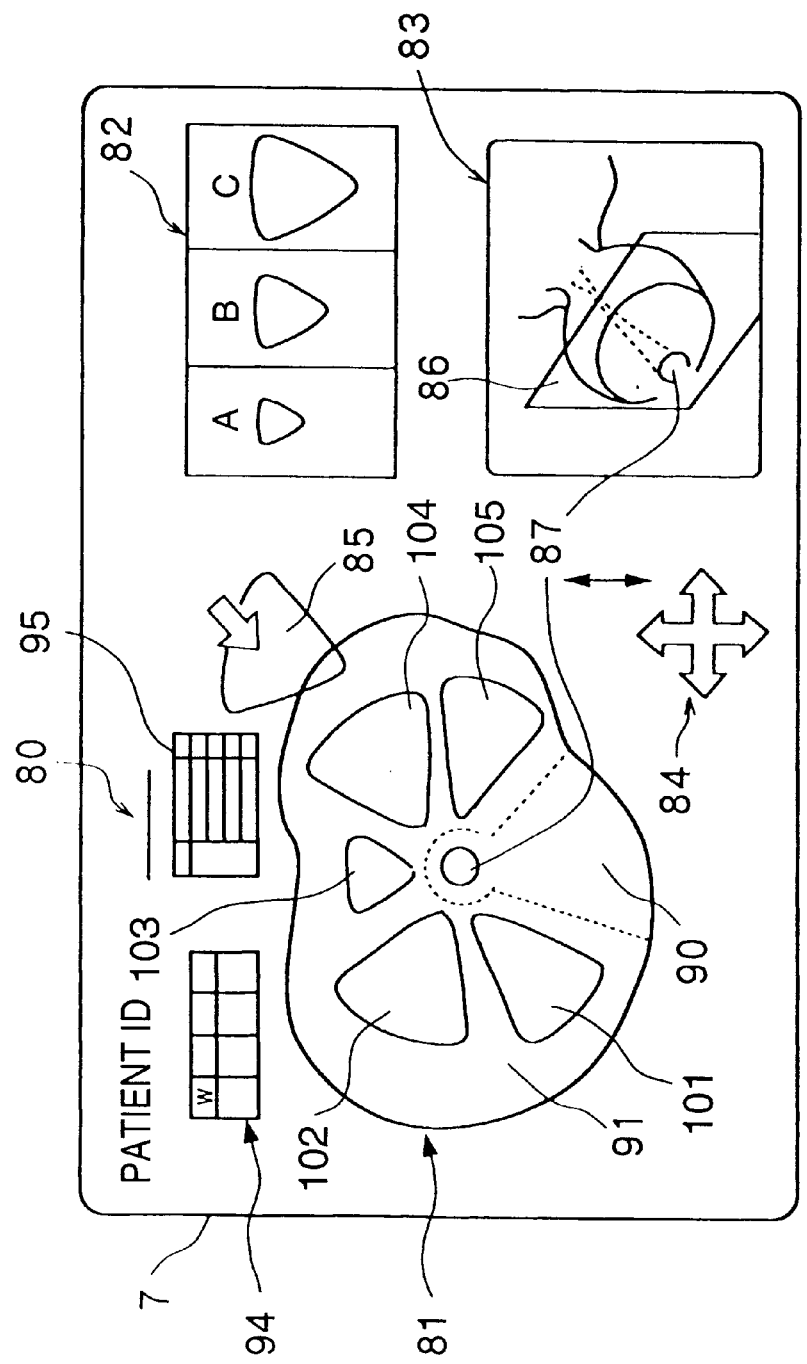
FIG. 8 is a view showing a display example when a heating region according to the first embodiment is set.

FIG. 8 is a view showing a display example on a display unit 7. Reference numeral 83 denotes a stereoscopic display example of a prostate. By using a cursor key 84 displayed on the screen, the position of a slice 86 of this stereoscopic image can be moved back and forth in a direction substantially perpendicular to a virtual urethra 87. A sectional shape cut by this slice 86 is displayed as indicated by 81 (step S3) Reference numeral 87 denotes a virtual urethra when the main body 110 is inserted; 80, a patient ID input/display area; 94, a laser irradiation condition display area; and 95, an area for displaying irradiation angles (to be described later) corresponding to different templates.

The flow then advances to step S4 to set non-heating regions (not to be irradiated with a laser beam) in this sectional shape 81. The non-heating regions include a preservation region around the urethra 87, a preservation region near the perimeter of the prostate, and a region 90 for protecting vasa deferentia positioned below the prostate. These non-heating regions can be designated by drugging using a mouse cursor or the like. Also, the thicknesses of the preservation regions around the urethra and near the perimeter of the prostate can be set by numerical values input from a keyboard or the like.

In step S5, a region in the sectional shape 81 except for the non-heating regions designated in step S4 is set as a target heating region 91, and a heating region to be actually heated is set in this target heating region 91.

As shown in FIG. 1, a region heated by irradiation with a laser beam in a human body 20 has a fan shape spreading outward when viewed from a laser beam source. This is so because a laser beam propagating in a human body diffuses in the body and circulating cooling water has a cooling effect. The size of this fan shape is changed in accordance with the energy, irradiation time, and the like of a laser beam. Accordingly, as indicated by a pallet 82 in FIG. 8, various fan-shaped heating range identifiers (A) to (C) (to be referred to as templates hereinafter) are prepared. By placing each template in the target heating region of the sectional shape 81 by drugging as indicated by 85, the heating policy for this target heating region can be determined or simulated. Assume that the memory 9 prestores information such as the irradiation energy, the irradiation time, the flow rate and temperature of cooling water, and the moving velocity of a reflecting portion in one-to-one correspondence with these templates of various sizes.

Figure 7:
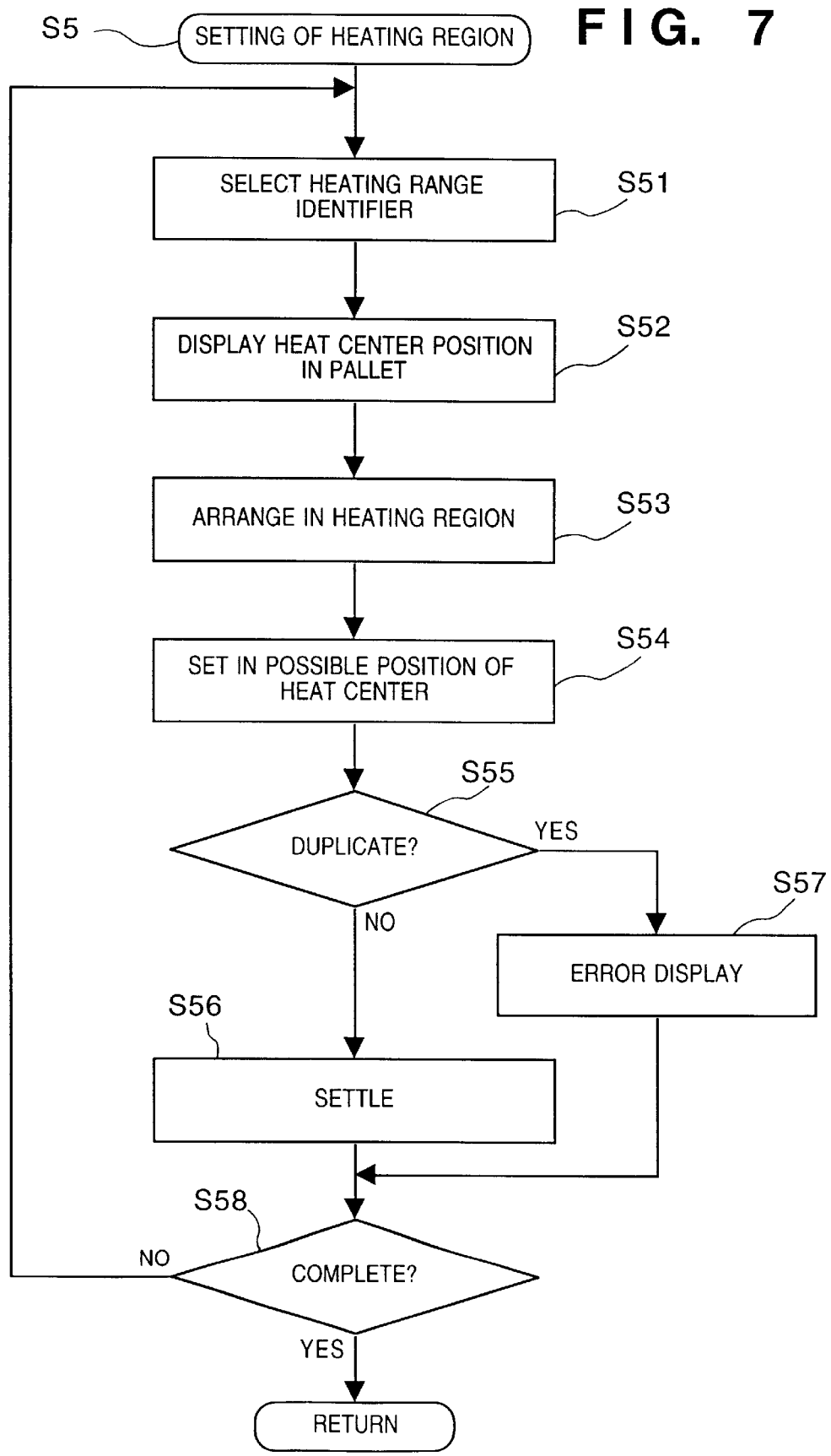
FIG. 7 is a flow chart showing a heating region setting process in step S5 of FIG. 6.

Details of this heating region setting process in step S5 are shown in a flow chart of FIG. 7.

Figure 9:
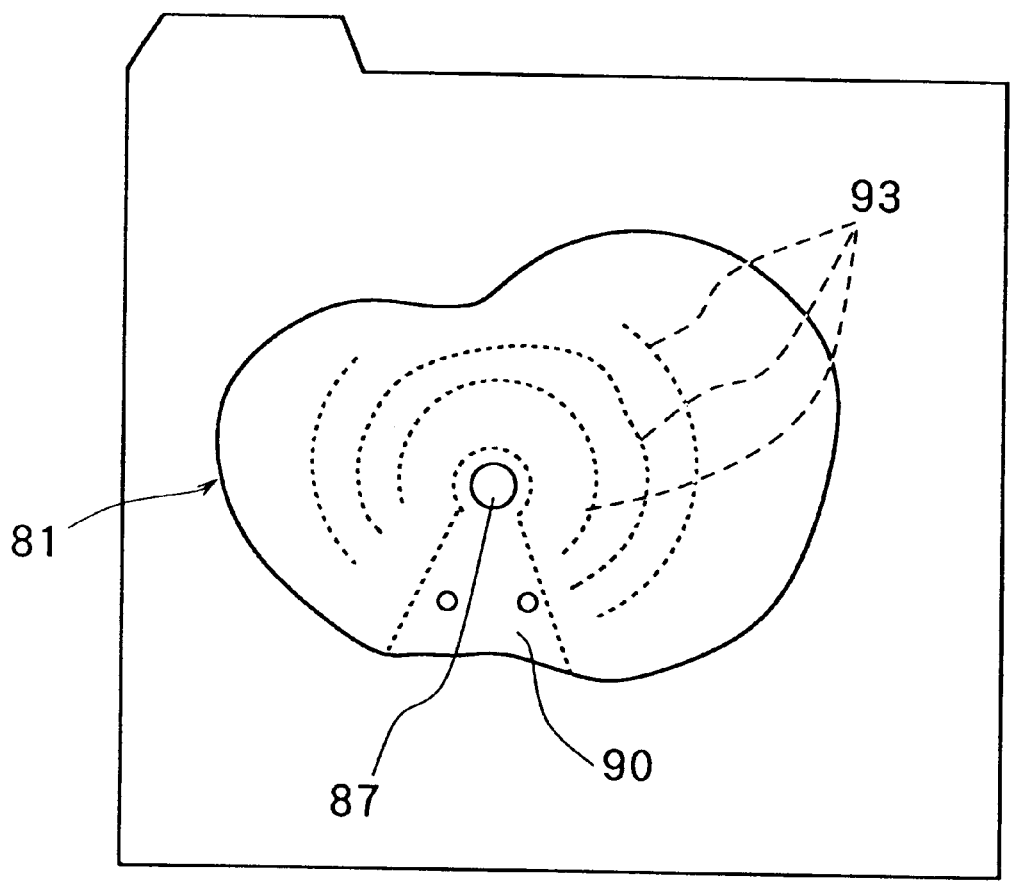
FIG. 9 is a view for explaining a settable position of a pallet.

Referring to FIG. 7, in step S51, one of the templates A to C in the pallet 82 is selected. Subsequently, as shown in FIG. 9, in accordance with this selected template, virtual lines 93 for positioning a highest-temperature point, i.e., a heat center of this template are displayed (S52). The selected template is moved to the target heating region 91 by drugging using the mouse or the like (S53). Consequently, as indicated by 81 in FIG. 8, the drugged template is positioned on the virtual lines 93, and a narrow portion (the pivot of the fan) of this template is pointed in the direction of the urethra 87.

In step S55, whether the template placed duplicates other templates already set is checked. If YES in step S55, error display is performed in step S57. If NO in step S56, the designated template is settled in the set position. In step S58, information indicating whether the template setting process is completed is displayed. If the process is completed, this flow is terminated. If the process is not completed, the flow returns to step S51 to reexecute the above process. In this manner, the operator properly selects a template from the templates A, B, and C (large, medium, and small) and places it in the target heating region 91 such that this target heating region 91 is entirely heated appropriately. Furthermore, the operator repeatedly adjusts the positions of already set templates until a desired three-dimensional arrangement is obtained. When the desired arrangement is finally obtained, the operator terminates the process.

The flow then advances to step S6 in FIG. 6 to set heating conditions. In step S7, thermal therapy is performed by laser beam irradiation in accordance with the set conditions.

FIG. 10 is a view showing set conditions such as laser irradiation conditions and a coolant corresponding to each of the templates A to C in the pallet 82 of FIG. 8. These set conditions can also be prestored in the memory 9. When one of templates 101 to 105 arranged in the target heating region 91 is chosen (FIG. 8) after the process shown in the flow chart of FIG. 7 is completed (after the desired arrangement is finally settled), the display unit 7 displays laser irradiation conditions 94 (corresponding to FIGS. 10 and 13) corresponding to the template.

Referring to FIG. 10, "LASER POWER" is the generation power (W) of a laser beam generated by a laser beam generator 2. "IRRADIATION TIME" is the laser beam irradiation time (sec). "COOLANT FLOW RATE" is the flow rate (ml/min) of a coolant supplied from a coolant supply unit 4. "DRIVING VELOCITY" is the velocity at which a reflecting portion 111 described previously is moved back and forth, and its unit is (round trips/sec). In addition, the temperature of the coolant and the like can also be included.

Second Embodiment

The second embodiment in which a laser irradiation apparatus is operated on the basis of a heating region and a non-heating region 90 obtained in the above first embodiment will be described below.

An operator causes this laser irradiation apparatus to detect a center y0 (a substantially bisecting angle of the non-heating region 90) of the angle of the non-heating region 90. Subsequently, the operator inserts an endoscope 180 into a catheter to confirm an operation field and confirm the central angle y0 of the non-heating region 90 (FIG. 8). The operator then resets an azimuth sensor 1200 (FIGS. 12A and 12B) to be described later to detect an angle of 0°.

A display unit 7 displays templates 101 to 105 (FIG. 8), the non-heating region 90, a diseased part (prostate) central preservation region (near a urethra), a diseased part (prostate) perimeter preservation region, an irradiation angle, and irradiation conditions 94 corresponding to a selected template. The irradiation angle is an angle formed by lines connecting the center y0, the pivot of the fan (template), and the heat center.

The angle of the catheter in the direction of the irradiation angle is changed automatically or manually, and laser beam irradiation is performed (S7 in FIG. 6). The operator can also adjust the irradiation conditions 94 in accordance with his or her taste.

Figure 11:
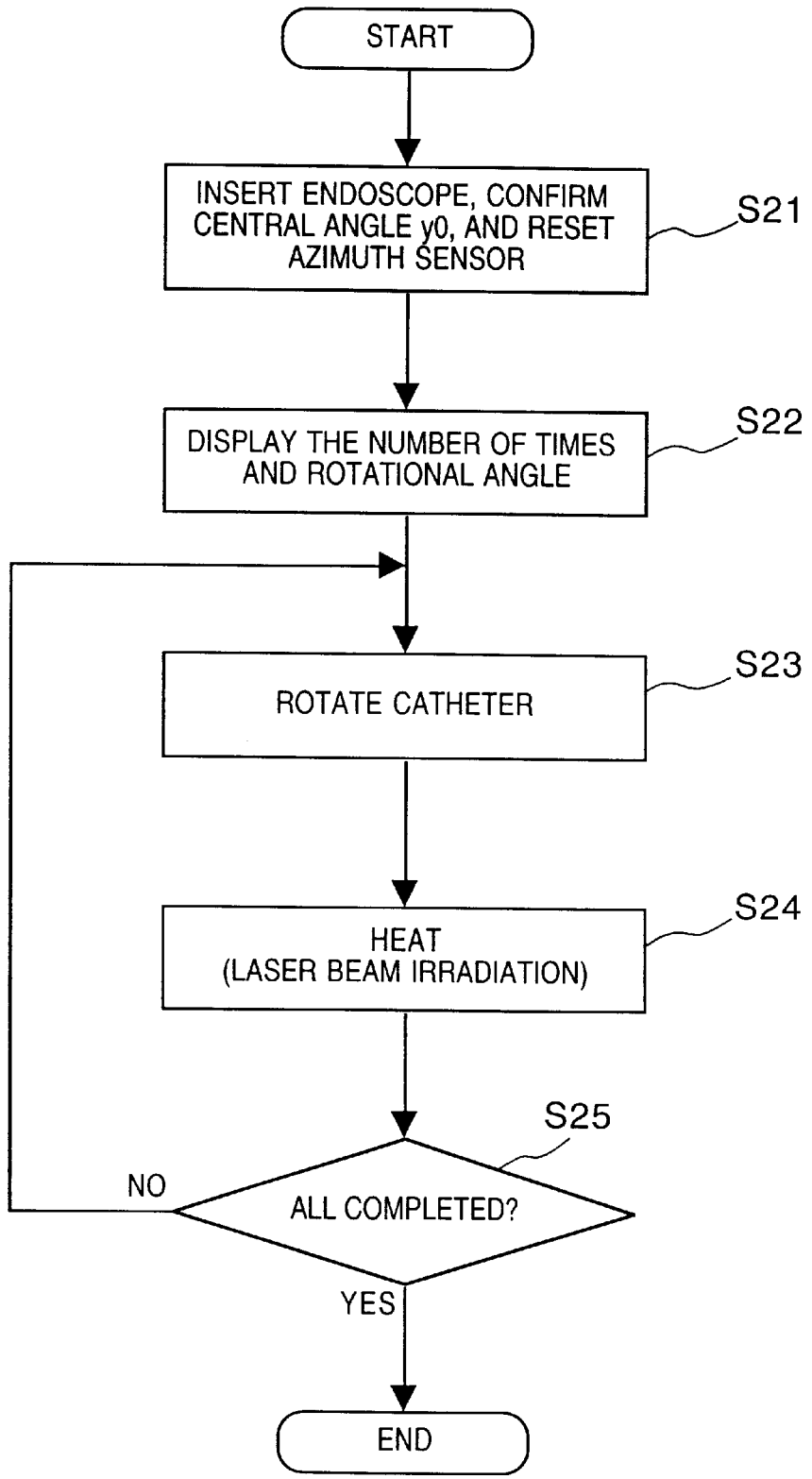
FIG. 11 is a flow chart for explaining a heating process using a medical laser irradiation apparatus of the second embodiment of the present invention.

FIG. 11 is a flow chart for explaining a laser irradiation process including operations by an operator.

In step S21, the operator causes this laser irradiation apparatus 10 to detect the central angle y0 of the non-heating region 90 obtained in the first embodiment. The operator inserts the endoscope 180 into a main body 110 of a catheter 1 to confirm an operation field, and resets the azimuth sensor 1200 (FIGS. 12A and 12B) for sensing the angle of the catheter 1 to 0°. In step S22, the templates 101 to 105 arranged as explained in FIG. 8 are displayed, and the operator first selects the template 101 by using a cursor. Consequently, the display unit 7 displays the irradiation conditions 94 and an irradiation angle 95 corresponding to the template 101. The flow advances to step S23 to rotate the main body 110 of the catheter through this irradiation angle in order to heat a region indicated by the first template 101. This rotation can be manually done by the operator. Alternatively, when the apparatus includes a catheter rotating device 1201 to be described later with reference to FIGS. 12A and 12B, the main body 110 can be automatically rotated in accordance with the rotational angle by this rotating device 1201. When the irradiation position of a laser beam is thus accurately positioned on the template 101, the flow advances to step S24, and a laser beam generator 2 generates a laser beam. This laser beam irradiates a human body 20 while a reflecting portion 111 is moved as described earlier. The operator can also adjust the irradiation conditions 94 before the irradiation. When the irradiation of the laser beam by the template is completed, i.e., when the thermal therapy is completed, the flow advances to step S25 to check whether all regions corresponding to the templates 101 to 105 are completely thermally treated. If NO in step S25, the flow returns to step S23 to select the next template and execute the above process. If heating regions corresponding to all templates are completely heated, the process is completed.

Figure 12:
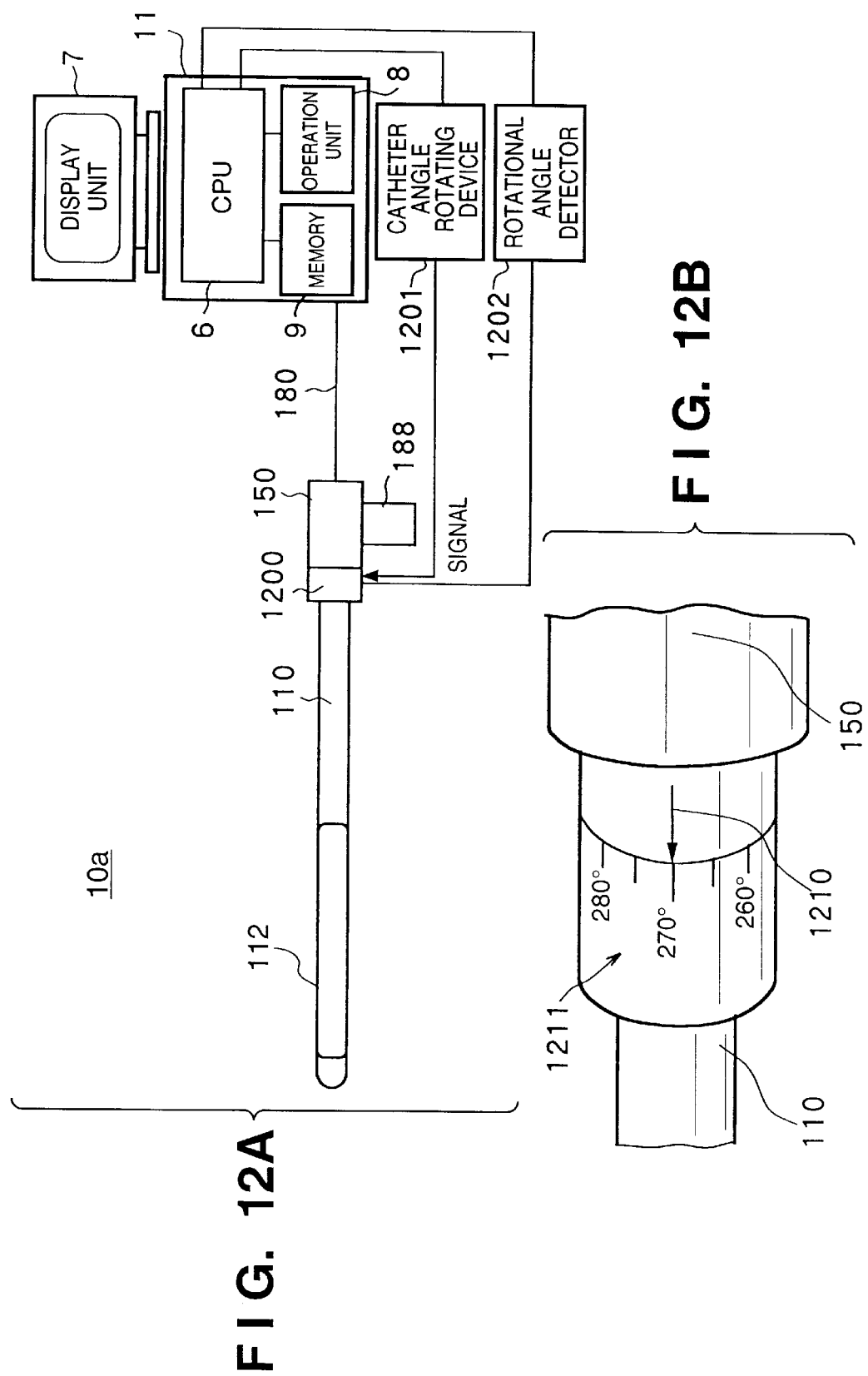
FIGS. 12A and 12B are a block diagram showing the arrangement of the medical laser irradiation apparatus of the second embodiment of the present invention and a view for explaining a rotational angle setting device, respectively.

FIG. 12A is a block diagram showing the arrangement of a laser irradiation apparatus 10a capable of automatically rotating the catheter 1 in accordance with the set position of a template.

FIG. 12B is a view for explaining an angle setting device for manually setting the rotational angle of the main body 110 of the catheter, as a modification to the second embodiment. Note that FIG. 12A shows only characteristic portions of this second embodiment, so the laser beam generator 2, the driving unit power supply 3, and the coolant supply unit 4 shown in FIG. 1 described earlier are not illustrated.

In FIG. 12A, reference numeral 1201 denotes a catheter angle rotating device. In accordance with an instruction from a controller 11, this catheter angle rotating device 1201 can change the rotational angle of the catheter to the designated angle. A rotational angle detector 1202 detects the rotational angle of the catheter main body 110 on the basis of an azimuth angle sensed by the azimuth sensor 1200.

FIG. 12B shows a rotational angle setting unit inserted between a driving unit 150 and the main body 110 of the catheter 1. The position of an angle set scale 1211 pointed by an arrow 1210 indicates a currently set rotational angle of the catheter 1. In the example shown in FIG. 12B, this angle is 270°.

The endoscope 180 used in this embodiment has a sighting device. When a reset reference line at 0° is aligned with substantially the center of the non-heating region 90 and the azimuth sensor 1200 is reset in this state, substantially the center of this non-heating region 90 is set as an angle of 0°.

In the above second embodiment, in step S24 of the flow chart in FIG. 11, the display unit 7 can also display a currently irradiated heating region corresponding to a template in a distinguishable manner. Furthermore, the number of times of heating or a current operation such as "heating preparations", "heating", or "heating complete" can be displayed.

Figures 13, 14:
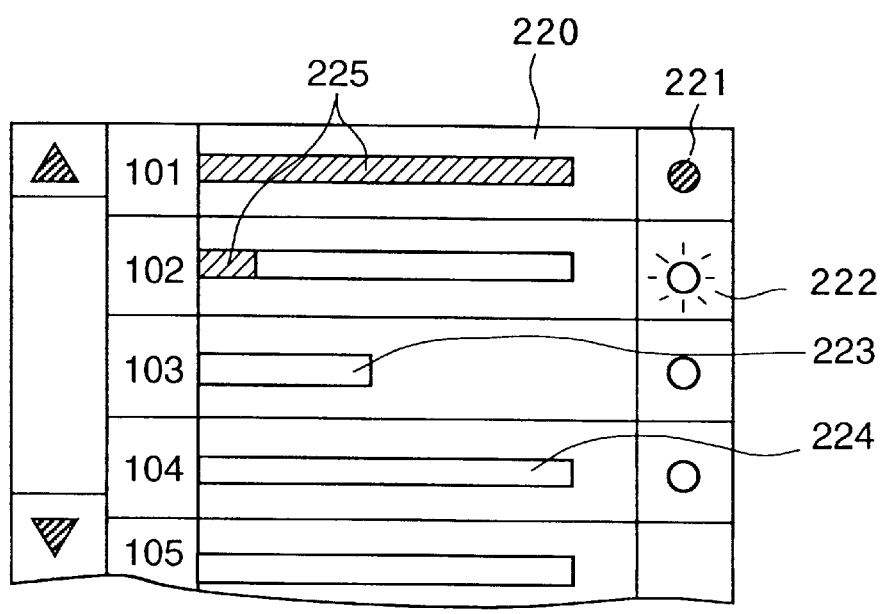
FIG. 13 is a view showing a display example of irradiation conditions of a heating region corresponding to a certain pallet.
FIG. 14 is a display example of irradiation states of heating regions corresponding to different pallets.

FIG. 13 is a view showing a display example of a window for displaying the laser irradiation state and the set states of a coolant and the like when a laser beam is irradiated to a heating region corresponding to each template. Referring to FIG. 13, parameters when a portion indicated by the template 102 in FIG. 8 is irradiated with a laser are displayed by numerical values or graphs. The individual display units in FIG. 13 correspond to the laser beam generation power (W), the coolant flow rate (ml/min), and the laser beam irradiation time (time: sec) in FIG. 10 and the temperature of the colloant (° C.). In addition, the driving velocity (round trips/sec) shown in FIG. 10 can also be displayed.

FIG. 14 is a view showing status display examples respectively corresponding to the templates 101 to 105 shown in FIG. 8. Reference numeral 220 denotes a bar graph indicating the passing time; 221, an indication of irradiation completion; and 222, an indication that the region is currently being irradiated with a laser. That is, the irradiation time is set for each template, and the whole irradiation time is indicated by a bar graph. A portion 225 indicating the elapsed part of the irradiation time is displayed in different color or brightness. Accordingly, FIG. 14 shows that a region corresponding to the template 101 is completely irradiated, a region corresponding to the template 102 is currently being irradiated with a laser, and approximately ⅙ the entire region is completely irradiated. Also, it is readily understandable from FIG. 14 that regions corresponding to the templates 103, 104 and 105 have not been irradiated with a laser yet. Note that this window can also be displayed instead of the angle display 95, or in another area, on the screen of the display unit 7 shown in FIG. 8.

As described above, an accurate therapeutic policy can be simulated or determined by arranging templates without imposing a burden on a patient. Furthermore, the second embodiment can accurately perform thermal therapy on a diseased part by controlling the rotational angle of the catheter or the irradiation of a laser beam either automatically or manually, thereby preventing duplication of laser irradiation regions or the formation of a region unirradiated with a laser.

Figure 15:
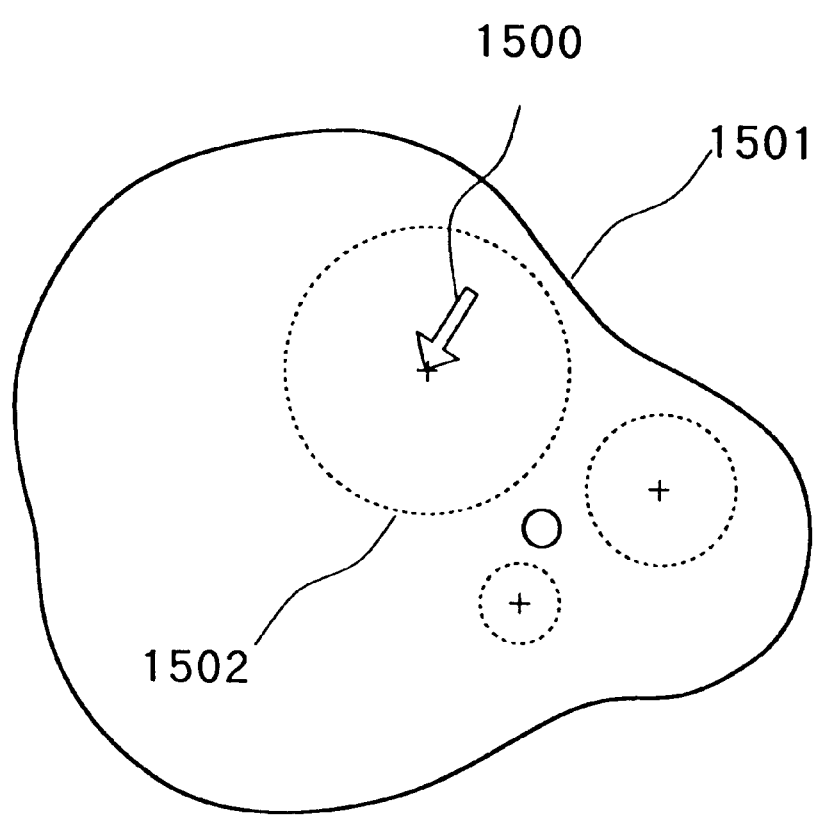
FIG. 15 is a view for explaining a heating region setting process of another embodiment.

In the previous embodiments, heating regions are set in a target heating region by arranging templates. However, the present invention is not restricted to these embodiments. For example, as shown in FIG. 15, the central heating point can be designated in a displayed sectional area 1501 by using a mouse cursor 1500 to display a heating range 1502 (necrotic range) in the tissue. The size of this necrotic range is calculated in accordance with a conditional expression contained in the controller 11, e.g., a conditional expression obtained from clinical data.

Third Embodiment

The characteristic features of a medical laser irradiation apparatus according to the third embodiment will be described below. This medical laser irradiation apparatus is a medical laser irradiation apparatus 10, explained with reference to FIGS. 1 to 5, by which a main body 110 is inserted into a urethra to perform irradiation of a laser beam into a prostate around the urethra, thereby treating BPH; benign prostatic hyperplasia.

Figure 16:
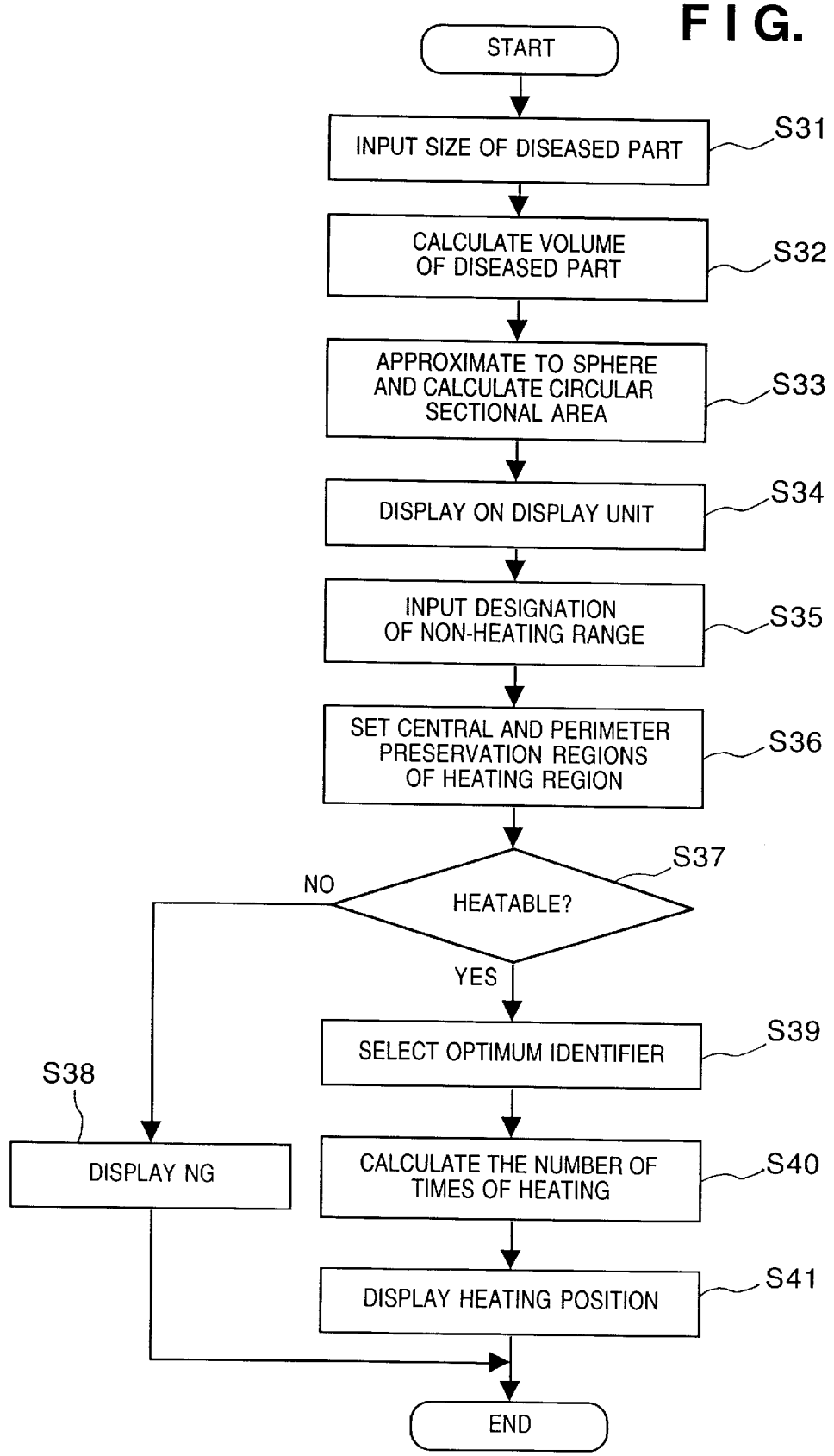
FIG. 16 is a flow chart showing a process of determining the number of times of heating and a heating position by a medical laser irradiation apparatus of the third embodiment of the present invention.

FIG. 16 is a flow chart showing a process of calculating an irradiation position in the medical laser irradiation apparatus 10 of the third embodiment. A control program for executing this process is stored in a memory 9 of a controller 11 and executed under the control of a CPU 6.

In step S31, the size of a diseased part to be treated is input from an operation unit 8. That is, on the basis of diagnostic data such as transurethral ultrasonic diagnosis, transabdominal ultrasonic diagnosis, transrectal ultrasonic diagnosis, MRI, and X-ray CT, three-dimensional lengths x, y, and z of the diseased part are measured, and an operator manually inputs the measurement results from the operation unit 8. It is also possible to directly input an image sensed by any of these methods and automatically measure and input the position and size of the diseased part. When the position/size information of the diseased part is thus input, the flow advances to step S32 to calculate the volume of the diseased part on the basis of the position/size information. In step S33, the calculated diseased part volume is approximated to a sphere, and a sectional (circular) shape having the largest area of the sphere is obtained. This shape is displayed on a display unit 7 (step S34).

Figure 17:
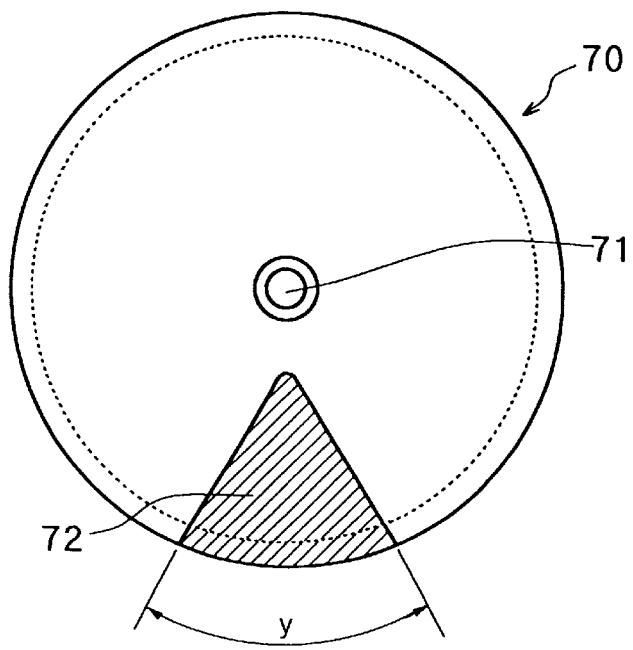
FIG. 17 is a view showing a display example in which a diseased part is approximated to a circle.

In step S35, the operator designates a range within which no irradiation with a laser beam is performed. That is, as shown in FIG. 17, a non-heating range 72 for protecting vasa deferentia (not shown) positioned below a urethra 71 is designated. FIG. 17 is a view showing an example of the circular data displayed on the display unit 7 in step S34. This non-heating range can be designated by a pointing device using a mouse cursor or the like displayed on the display unit 7. Alternatively, on the basis of the displayed shape, the position, size, and angle y can be input from a keyboard or the like.

The flow then advances to step S36 to designate a central preservation region 73 near the urethra 71 and a perimeter preservation region 74 of the prostate. These preservation regions 73 and 74 and the non-heating region 72 described above are displayed on the display unit 7 (FIG. 18). Reference numeral 75 denotes a target heating region.

Figure 19B:
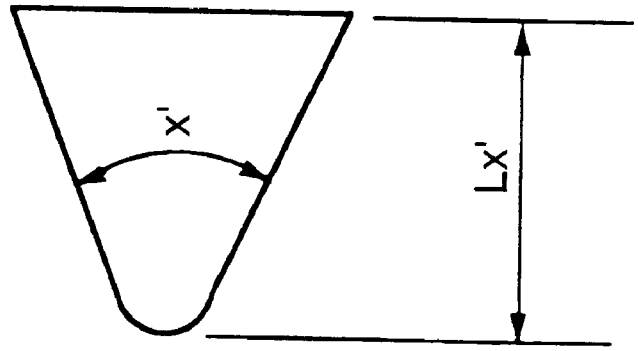
FIGS. 19A and 19B are views for explaining a region to be heated by laser irradiation.
Figure 19A:
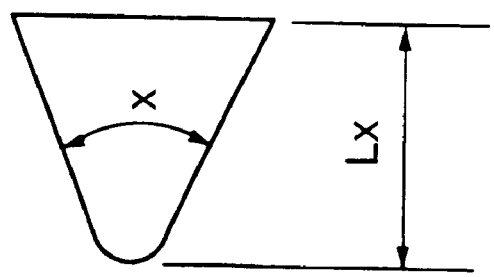

In step S37, whether the target heating region 75 set in step S36 can be heated is checked. A range to be heated by irradiation with a laser beam has a shape close to a fan as shown in FIG. 19A or 19B, i.e., has a shape spreading into the shape of a fan having an angle x and a length Lx when viewed from the irradiation side of a laser beam. This therapeutic condition (heating range) is determined by the laser irradiation conditions, the set conditions of a coolant, and the set conditions of the driving velocity. FIGS. 19A and 19B show two therapeutic conditions (heating ranges).

FIG. 22 is a view showing laser irradiation conditions and coolant set conditions respectively (A and B) corresponding to the heating range identifiers (to be referred to as identifiers hereinafter) shown in FIGS. 19A and 19B. These set conditions are stored in the memory 9 of the controller 11, and therapeutic conditions corresponding to a selected heating range are displayed on the display unit 7.

Referring to FIG. 22, "LASER POWER" is the generation output (W) of a laser beam generated by a laser beam generator 2. "IRRADIATION TIME" is the laser beam irradiation time (sec). "COOLANT FLOW RATE" is the flow rate (ml/min) of a coolant supplied from a coolant supply unit 4. "DRIVING VELOCITY" is the velocity at which a reflecting portion 111 described previously is moved back and forth, and its unit is (round trips/sec). In addition, the temperature of the coolant and the like can also be included.

Figure 18:
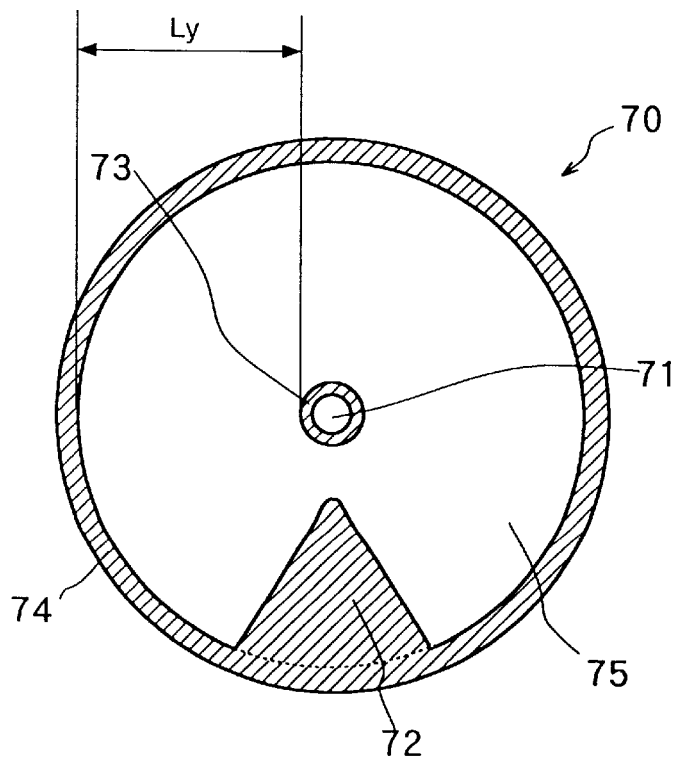
FIG. 18 is a view showing a display example in which a non-heating region is set in the diseased part approximated to a circle in FIG. 17.

As shown in FIG. 18, letting Ly shows the depth of the target heating region 75, this target heating region 75 can be heated if the minimum length Lx (FIG. 19) of an identifier satisfies Lx≦Ly. If not, either the central preservation region 73 or the perimeter preservation region 74 is heated by a laser beam, so it is determined that this shape cannot be heated. In this case, the flow advances to step S38 to display "NG", indicating that heating is impossible, on the display unit 7.

On the other hand, if Lx≦Ly is met and heating is possible, the flow advances to step S39, and an optimum identifier is chosen in accordance with the size of the heating region. In step S40, the number F of times of heating is calculated from the selected identifier. This F can be calculated by F=(360−y)/x. If this (360−y)/x is divisible, the number of times of heating is F=(F−1) [times]. If (360−y)/x is indivisible, the figures below the decimal point are omitted.

Figure 20:
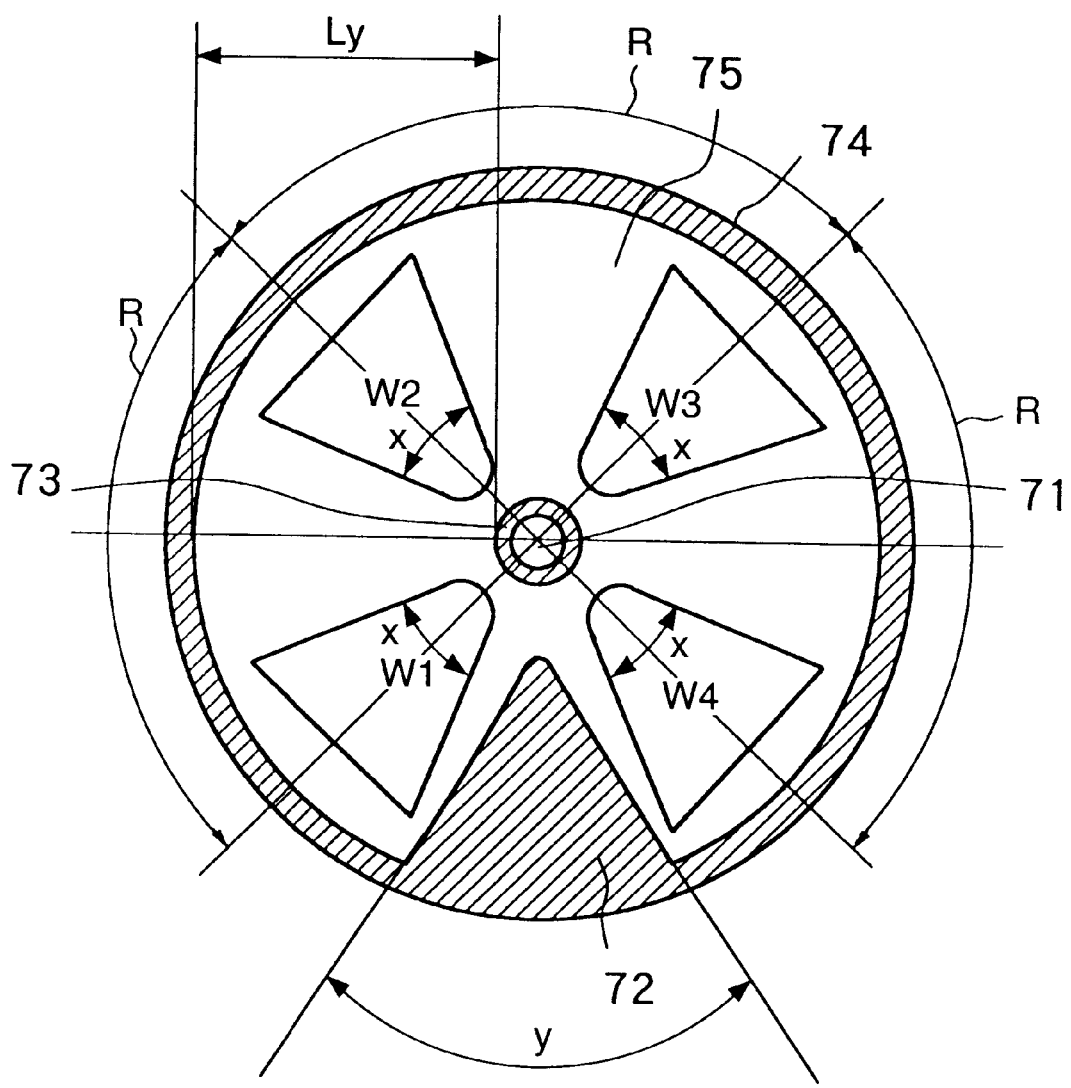
FIG. 20 is a view showing a display example in which a heating region is set by substantially equally dividing a heating region of a diseased part.

Subsequently, the flow advances to step S41 to obtain a heating position. Since it is desirable that the heating region 75 be divided as uniformly as possible before being irradiated with a laser beam, a uniform angle R of the heating region is first obtained. This angle can be calculated by R=(360−y)/F. As shown in FIG. 20, laser irradiation ranges are uniformly arranged in the heating region 75 on the basis of this uniform angle R. The result is displayed on the display unit 7. Accordingly, the operator can easily discriminate the number of times of heating and the heating position (angle).

In this third embodiment as described above, the number of heating times and the heating position can be automatically obtained by designating a non-heating region.

Fourth Embodiment

The fourth embodiment in which a laser irradiation apparatus is operated on the basis of the heating region, non-heating region, uniform angle, and the like obtained in the above third embodiment will be described below.

As described above with reference to FIGS. 19A and 19B, an operator causes this laser irradiation apparatus to detect a center y0 of the angle of a non-heating region 72. Subsequently, the operator inserts an endoscope 180 into a catheter to confirm an operation field and the central angle y0 of the non-heating region 72, and resets an azimuth sensor 1200 (above-mentioned) to confirm an angle of 0°.

The operator then causes a display unit 7 to display heating ranges W1 to W4 (FIG. 20) when the central angle y0 is 0°, a uniform angle R, the non-heating region 72, a diseased part central preservation region 73, a diseased part perimeter preservation region 74, and the number F of times of heating.

The operator presses a button to choose whether the diseased part is to be automatically or manually heated, changes the angle of the catheter in the direction of the angle R either automatically or manually, and irradiates a laser beam. The operator can also readjust the irradiation conditions in accordance with his or her taste.

Figure 21:
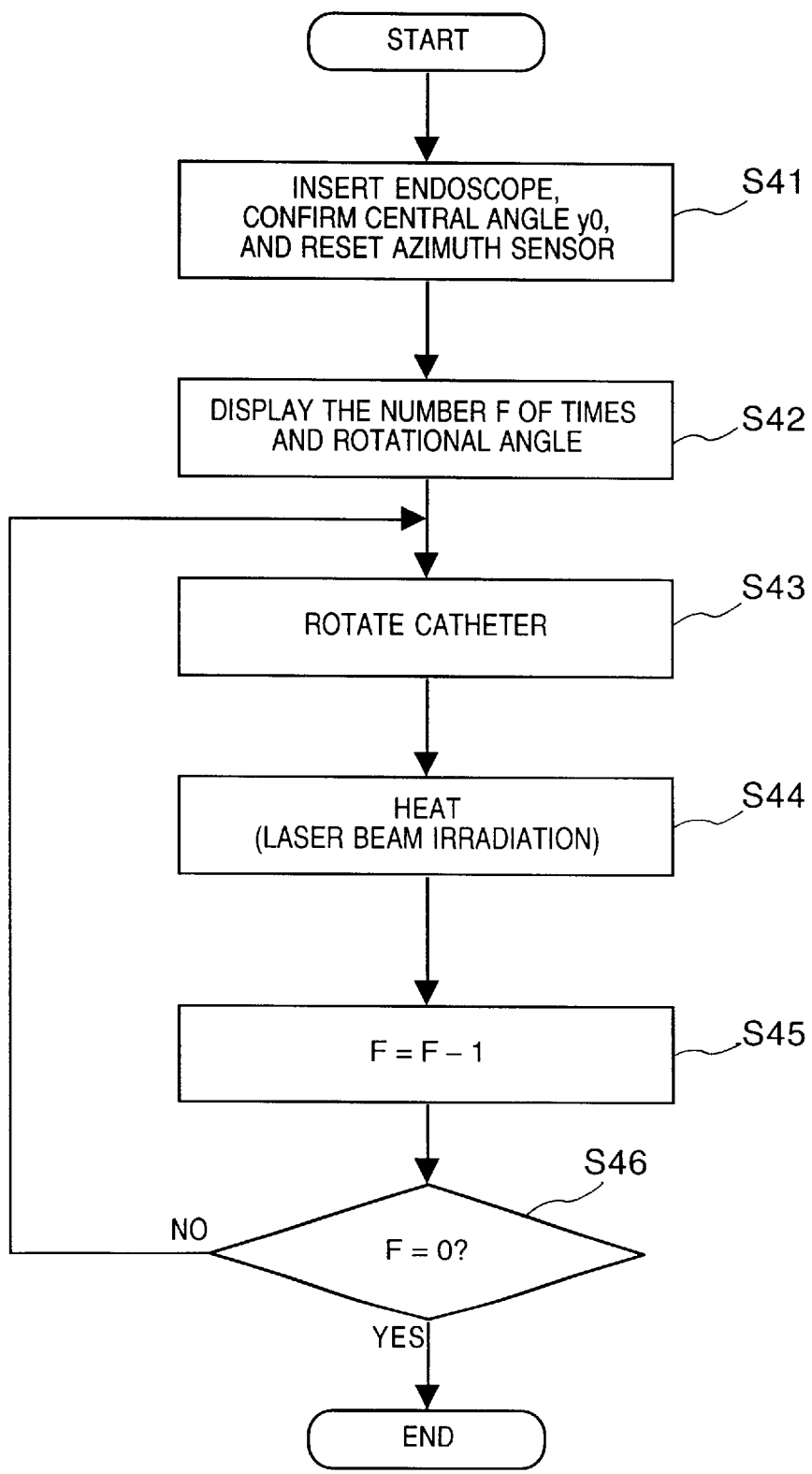
FIG. 21 is a flow chart for explaining a heating process using a medical laser irradiation apparatus of the fourth embodiment of the present invention.

FIG. 21 is a flow chart for explaining a laser irradiation process including operations by an operator according to the fourth embodiment of the present invention.

In step S41, an operator causes this laser irradiation apparatus to detect the central angle y0 of the non-heating region 72 obtained in the abovementioned third embodiment. The operator inserts the endoscope 180 into the catheter to confirm an operation field, and resets the azimuth sensor 1200 (FIG. 19A) for sensing the angle of the catheter to 0°. The flow advances to step S42 to display the number F of heating times, the rotational angle R, and the heating regions W1 to W4 obtained in the third embodiment on the display unit 7. In step S43, in accordance with this rotational angle R, the catheter is rotated the angle R (e.g., 45°) to heat the first heating region W1. This rotation can be done manually by the operator. Alternatively, when the apparatus includes a catheter angle rotating device 1201 described previously with reference to FIGS. 19A and 19B, the catheter can also be automatically rotated in accordance with the rotational angle by this rotating device 1201. When a laser beam irradiation position is thus accurately positioned in the heating region W1, in step S44 a laser generator 2 generates a laser beam, and this laser beam irradiates a human body 20 while a reflecting portion 111 is moved as described previously. When this heating region is completely irradiated with the laser beam, i.e., completely heated, the flow advances to step S45 to reduce the number F of times of heating by −1. In step S46, whether F=0 is checked. If NO in step S46, the flow returns to step S43, and the catheter is rotated this time 135° to heat the next heating region W2. When the number F of times of heating =0 and the heating regions W1 to W4 are completely heated, this process is completed.

When heating is performed at a uniform angle like this, information indicating that heating is impossible is displayed if the same position is to be again heated.

In this fourth embodiment as described above, optimum heating positions and an optimum number of times of heating of a diseased part can be obtained from the rotational angle R and the number F of times of heating obtained in the third embodiment described earlier. The diseased part can be heated by controlling the rotational angle of the catheter or the irradiation of a laser beam either automatically or manually in accordance with the obtained heating positions and number of times of heating.

In the above fourth embodiment, in step S44 of the flow chart in FIG. 21, a heating region currently being irradiated can also be displayed in a distinguishable manner on the display unit 7. Furthermore, the number of times of heating and a current operation such as "heating preparations", "heating", or "heating complete" can be displayed.

Also, as described above, if a certain heating region is to be again heated, "heating is impossible" can be displayed on the display unit 7.

Note that the endoscope 180 used in this embodiment has a sighting device. When a reset reference line at 0 is aligned with almost the center of the non-heating region 72 and the azimuth sensor 1200 is reset in this state, almost the central angle of this non-heating region 72 is set as 0°.

Fifth Embodiment

Figure 23:
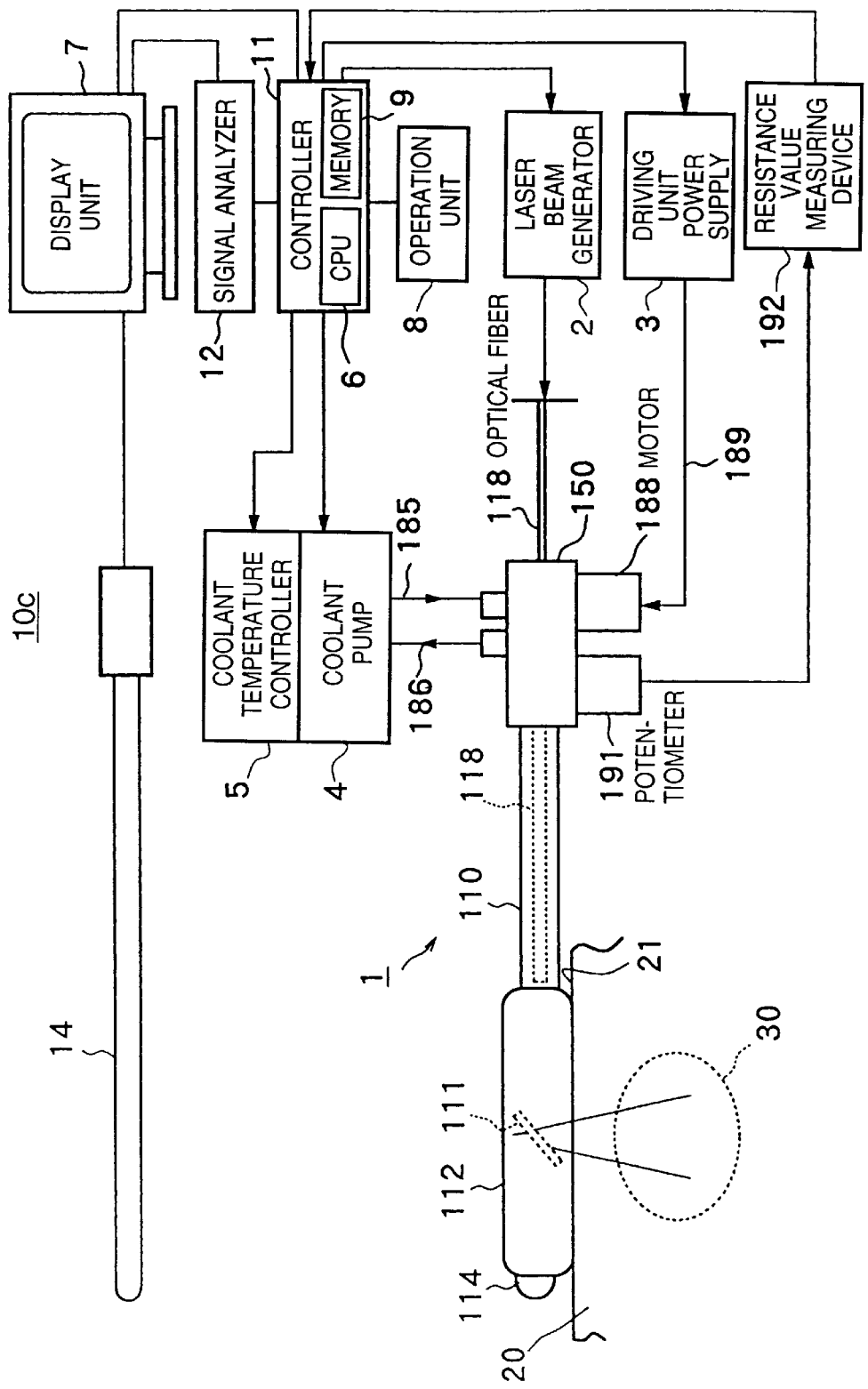
FIG. 23 is a block diagram showing the arrangement of a medical laser irradiation apparatus according to the fifth embodiment of the present invention.

FIG. 23 is a block diagram showing the arrangement of a medical heating apparatus 10c according to the fifth embodiment of the present invention. The same reference numerals as in FIG. 1 denote the same parts in FIG. 23.

Referring to FIG. 23, this medical heating apparatus 10c has a side-emission-type laser irradiation catheter 1 for irradiating a vital tissue with a laser beam. A main body 110 as a long insertion portion of the laser irradiation catheter 1 of this medical heating apparatus 10 is inserted into a human body. A reflecting portion 111 installed in this main body 110 irradiates a vital tissue 20 with a laser beam. For example, this medical heating apparatus 10 is used to treat BPH; benign prostatic hyperplasia or tumors such as various cancers. The construction of this laser irradiation catheter 1 will be described later with reference to FIG. 24. Reference numeral 2 denotes a laser beam generator for generating a laser beam; 3, a driving power supply for driving a motor 188; 4, a pump for supplying a coolant for cooling the catheter 1 into the catheter 1; 5, a temperature controller for controlling the temperature of the coolant in accordance with an instruction from a controller 11; 7, a display unit such as a CRT or a liquid crystal display; and 8, an operation unit including a keyboard and a pointing device such as a mouse. The controller 11 includes a CPU 6 such as a microprocessor and a memory 9 storing programs executed by the CPU 6 and various data. A signal analyzer 12 analyzes an image signal of a diseased part or the like of a human body obtained on the basis of an ultrasonic signal detected by an ultrasonic probe 14, and obtains the size and shape of the diseased part. A resistance value measuring device 192 reads the resistance value of a potentiometer 191 to detect the rotational angle of the catheter 1.

Figure 24:
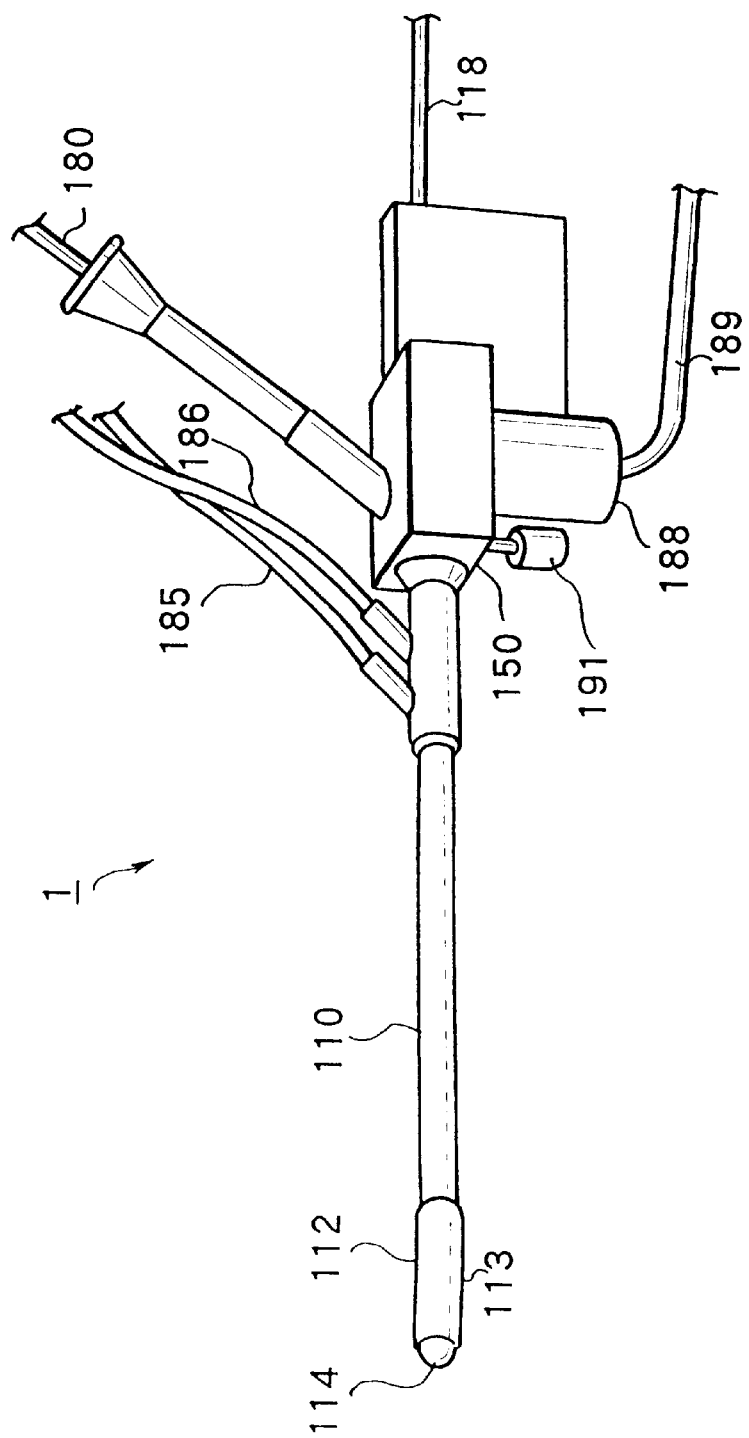
FIG. 24 is a perspective view showing the external appearance of a catheter of this embodiment.

FIG. 24 is a perspective view showing the external appearance of the laser irradiation catheter 1 according to this embodiment. The same reference numerals as in FIG. 23 denote the same parts in FIG. 24, and these parts will be described later. Note that the potentiometer 191 is for detecting the rotational angle of the catheter 1, and detects a relative angle from an initial value. This allows an operator to confirm the irradiation direction of a laser beam in a plane perpendicular to the axial direction of the main body 110. Note that this catheter 1 is also applicable to the previous embodiments.

In this apparatus, operations of a housing 112, an arm 116, and the reflecting portion 111 of the laser irradiation catheter 1 are the same as in the embodiment explained with reference to FIGS. 2 to 5, so a detailed description thereof will be omitted.

To thermally treat a prostatic disease by laser irradiation as described above, it is necessary to previously obtain information pertaining to the shape of the prostate. Therefore, the ultrasonic probe 14 capable of radial scan is inserted into a urethra near the prostate to obtain its shape.

In this apparatus, when the ultrasonic probe 14 is inserted into the urethra, the display unit 7 displays a two-dimensional ultrasonic image of a slice of the prostate.

FIGS. 25A to 25F are views showing the insertion positions of the ultrasonic probe 14 and tomographic images, corresponding to these insertion positions, displayed on the display unit 7. In each of FIGS. 25A to 25F, reference numeral 31 denotes a urinary bladder; 32, a urethral sphincter; 33, a prostate; and 34, a urethra.

Figure 25A:
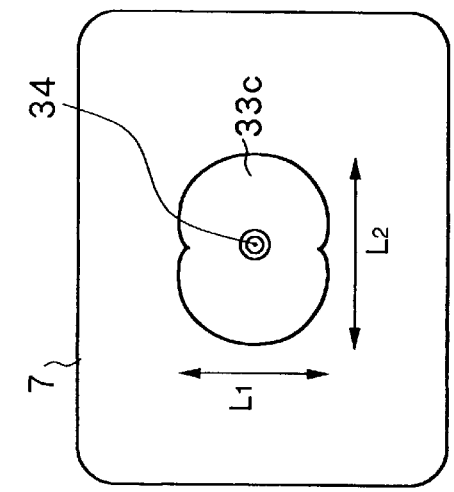
FIGS. 25A to 25F are views for explaining images of a prostate sensed by an ultrasonic probe in the fifth embodiment of the present invention.
Figure 25B:
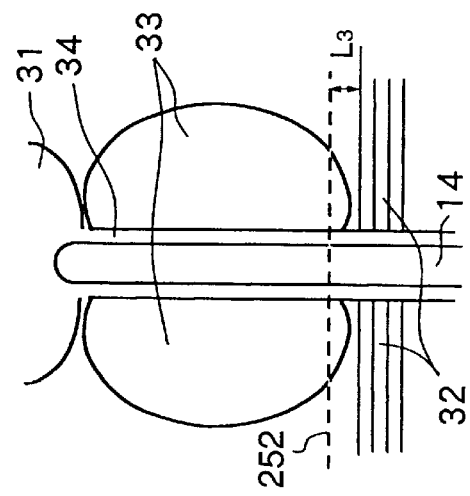
Figure 25C:
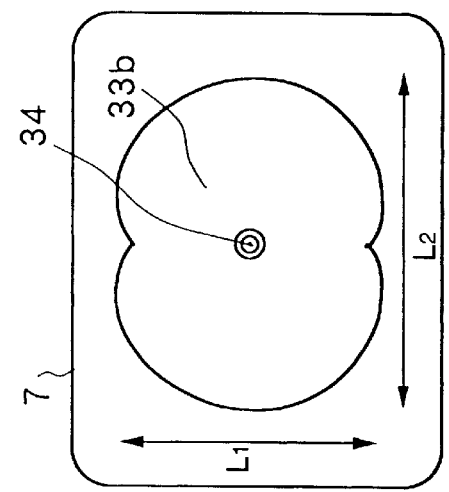
Figure 25D:
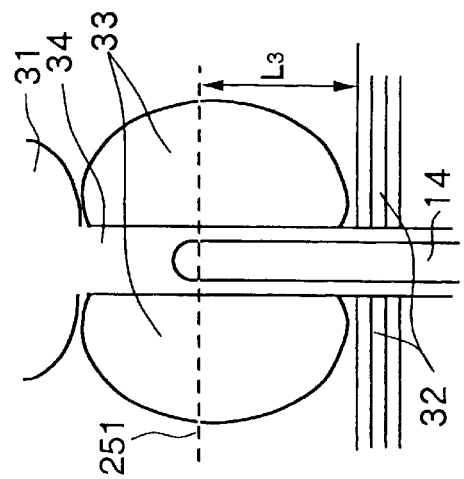
Figure 25E:
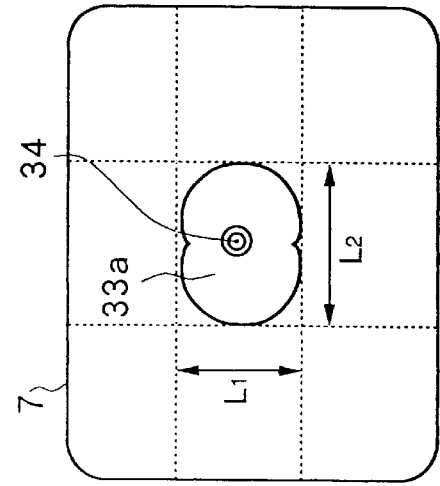
Figure 25F:
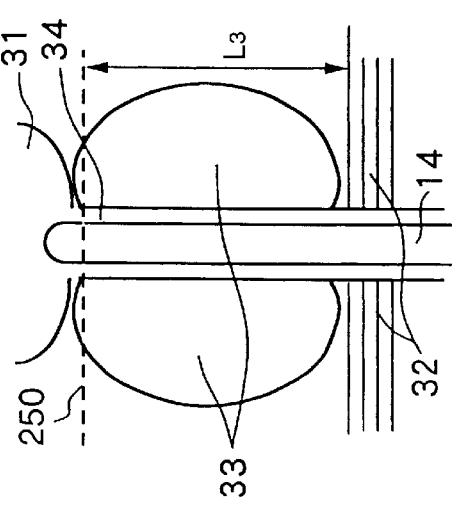

FIG. 25A shows an ultrasonic image 33a when the ultrasonic probe 14 is inserted to a deepest portion 250 of the urethra 34 as shown in FIG. 25B. FIG. 25C shows an ultrasonic image 33b when the ultrasonic probe 14 is inserted to an almost a center 251 of the prostate 33 as shown in FIG. 25D. FIG. 25E shows an ultrasonic image 33c when the ultrasonic probe 14 is inserted to a front portion 252 of the prostate 33. The signal analyzer 12 discriminates the shape of the cross section of the prostate 33 from the difference in the brightness or contrast of the ultrasonic image of the prostate obtained by the ultrasonic probe 14. The signal analyzer 12 analyzes a length L1 in the vertical direction and a length L2 in the horizontal direction of the slice of the prostate 33, preferably the cross-sectional shape of the prostate 33 at each insertion position, i.e., each measurement position (L3), and displays the results on the display unit 7. This allows an operator to understand the size, preferably the shape of the slice of the prostate 33 at the desired measurement position (L3).

The length L1 in the vertical direction and the length L2 in the horizontal direction of the slice of the prostate 33, preferably the cross-sectional shape of the prostate 33 can also be manually measured by using the operation unit 8. Also, the measurement position L3 can be obtained by measurement using a scale (not shown) formed on the ultrasonic probe to indicate the insertion depth. However, the measurement position L3 can also be obtained by attaching to the ultrasonic probe 14 a displacement sensor for sensing the insertion amount into a body cavity and receiving and analyzing a signal from this displacement sensor by the signal analyzer 12 or the like. By obtaining this measurement position L3, it is possible to confirm on an ultrasonic image the distance from a measurement position at which the boundary between the urinary bladder 31 and the prostate 33 appears to a measurement position at which the boundary between the prostate 33 and the urethral sphincter 32 appears. Consequently, information indicating the length in the direction of the urethra of the prostate 33 can be displayed on the display unit 7.

Figure 26:
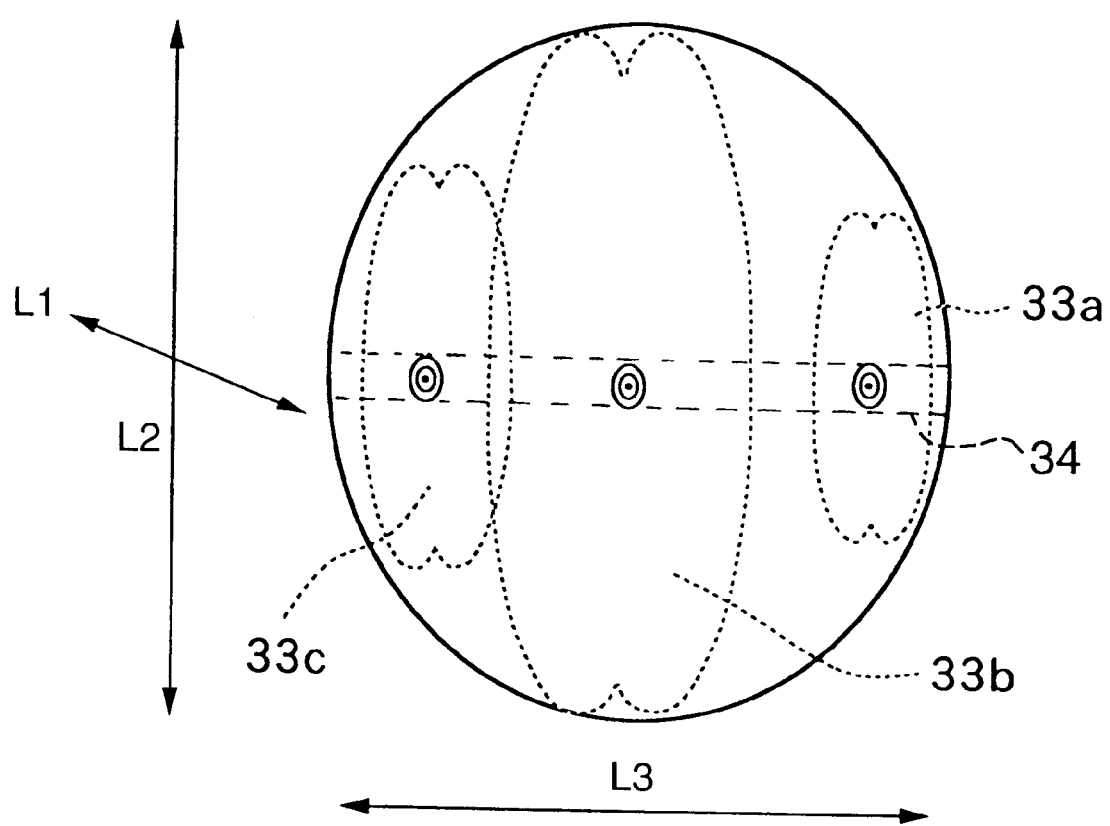
FIG. 26 is a view showing a three-dimensional model of a prostate based on an ultrasonic signal.

FIG. 26 is a view showing an example of a three-dimensional model, representing the shape of the prostate 33, formed on the basis of the relationship between the tomographic images shown in FIGS. 25A, 25C, and 25E and the corresponding measurement position (L3). The analysis of such an image signal is also performed by the signal analyzer 12.

The signal analyzer 12 need only numerically analyze the length L1 in the vertical direction and the length L2 in the horizontal direction of the slice of the prostate 33 and the length in the direction of the urethra of the prostate 33 and display the results on the display unit 7. However, the signal analyzer 12 preferably forms a three-dimensional figure approximated to an elliptic sphere, on the basis of the length L1 in the vertical direction and the length L2 in the horizontal direction of the slice of the prostate 33 and the length (L3) in the direction of the urethra of the prostate 33, and graphically displays the figure on the display unit 7. Also, by using computer software for constructing a three-dimensional image, which can be installed in the signal analyzer 12, slices of the prostate 33 at different measurement positions (L3) can be overlapped to form a more accurate three-dimensional image of the prostate 33. This three-dimensional image can also be manually formed using the operation unit 8. Note that the ultrasonic probe 14 can be inserted into the urethra 34 as described above and can also be inserted into a rectum. Note also that although this probe 14 can have a long shape, it can also have a flat shape or a curved shape pushed against the abdomen near the prostate.

Furthermore, although the scan scheme of the ultrasonic probe 14 is radial scan, it is also possible to perform scan in sector and linear directions to obtain and display the shapes of a slice of the prostate almost perpendicular to the urethra and a longitudinal section of the prostate almost parallel to the urethra.

Sixth Embodiment

Figure 27:
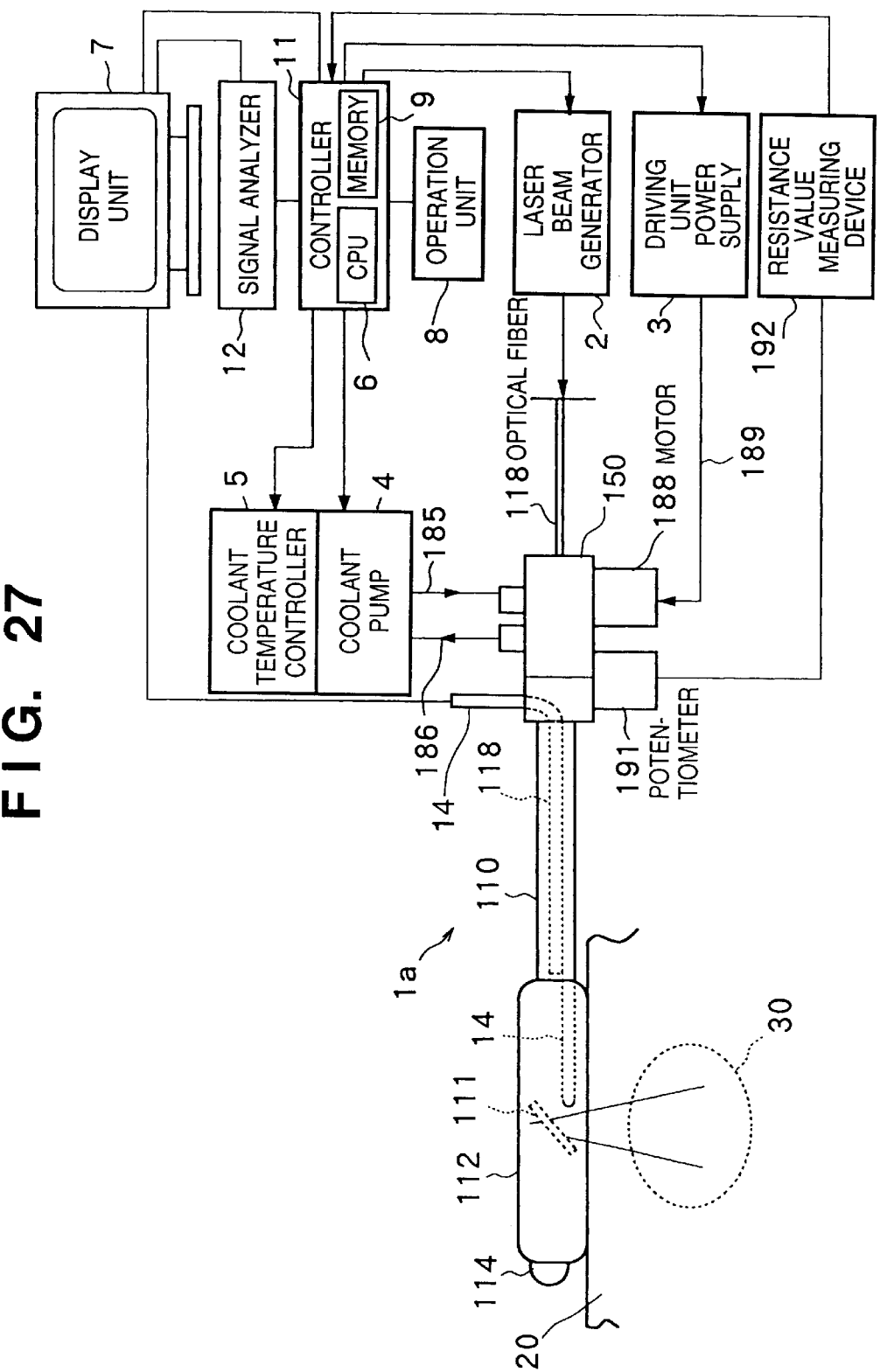
FIG. 27 is a block diagram showing the arrangement of a medical laser irradiation apparatus according to the sixth embodiment of the present invention.

FIG. 27 is a block diagram showing the arrangement of a medical heating apparatus according to the sixth embodiment of the present invention. The same reference numerals as in the abovementioned arrangement denote the same parts in FIG. 27, and a detailed description thereof will be omitted. This sixth embodiment is characterized in that an ultrasonic probe 14 is inserted into a main body 110 of a laser irradiation catheter 1a. When the diameter of the ultrasonic probe 14 is thus small, it can also be inserted through a lumen formed in the laser irradiation catheter 1a.

In the above fifth embodiment, the shape of a diseased part must be previously measured by inserting the ultrasonic probe 14 into a urethra or a rectum. In this sixth embodiment, however, the shape of a diseased part can be measured simultaneously with insertion of the catheter 1a for laser irradiation. This can reduce the burden on a patient.

Although the scan scheme of the ultrasonic probe 14 is radial scan, it is also possible to perform scan in sector and linear directions to obtain and display the shapes of a cross section of a prostate almost perpendicular to the urethra and a longitudinal section of the prostate almost parallel to the urethra.

Seventh Embodiment

Figure 28:
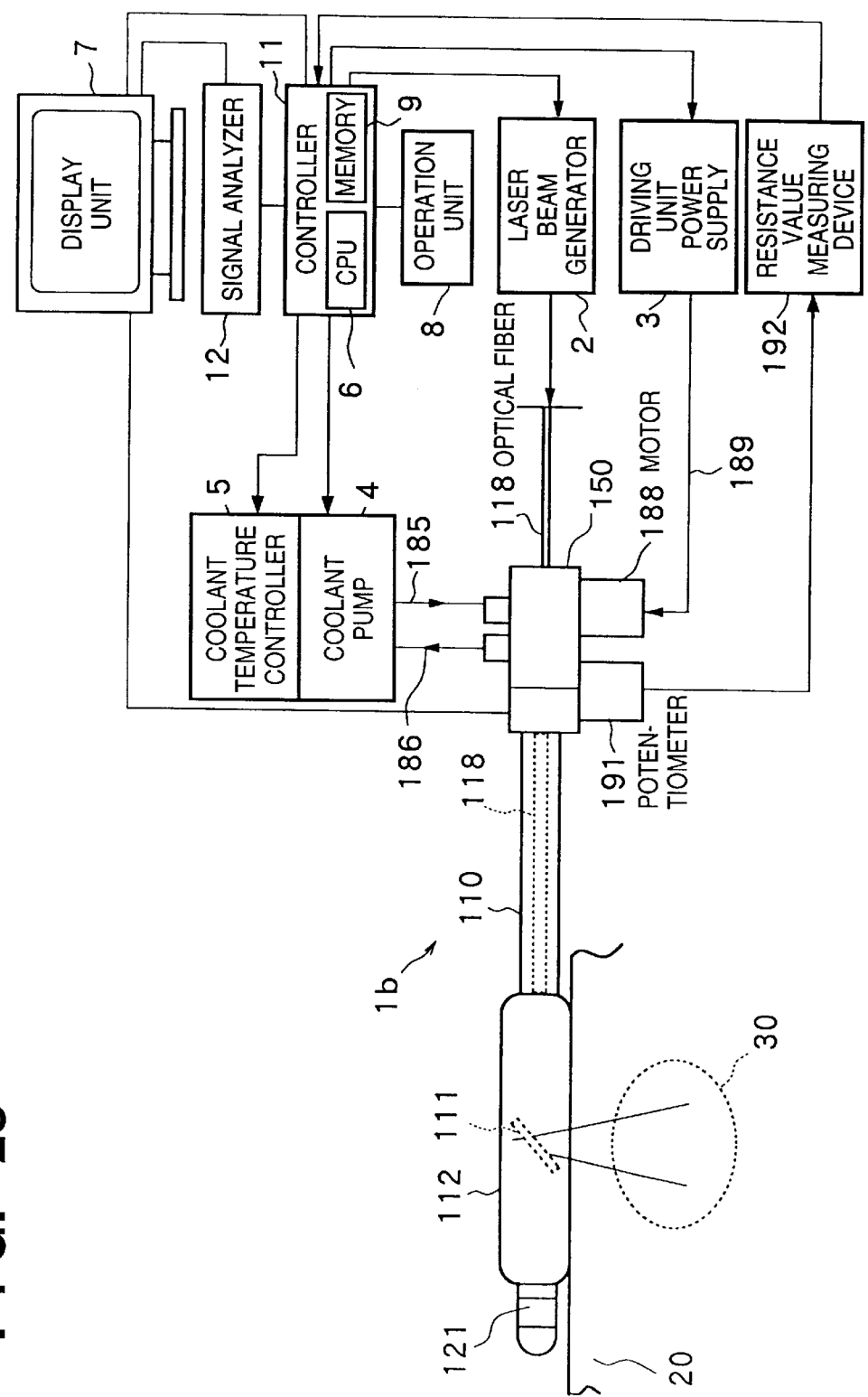
FIG. 28 is a block diagram showing the arrangement of a medical laser irradiation apparatus according to the seventh embodiment of the present invention.

FIG. 28 is a block diagram showing the arrangement of a medical laser irradiation apparatus according to the seventh embodiment of the present invention. The same reference numerals as in the abovementioned arrangement denote the same parts in FIG. 28, and a detailed description thereof will be omitted.

In this apparatus, an ultrasonic vibrator 121 is attached to a portion corresponding to the cap 114 (FIGS. 1, 23, and 27) at the distal end portion of a housing 112. The shape of a diseased part is measured on the basis of an ultrasonic wave radiated from this ultrasonic vibrator 121. The rest of the arrangement is basically the same as the abovementioned arrangement, so a detailed description thereof will be omitted.

Figure 29:
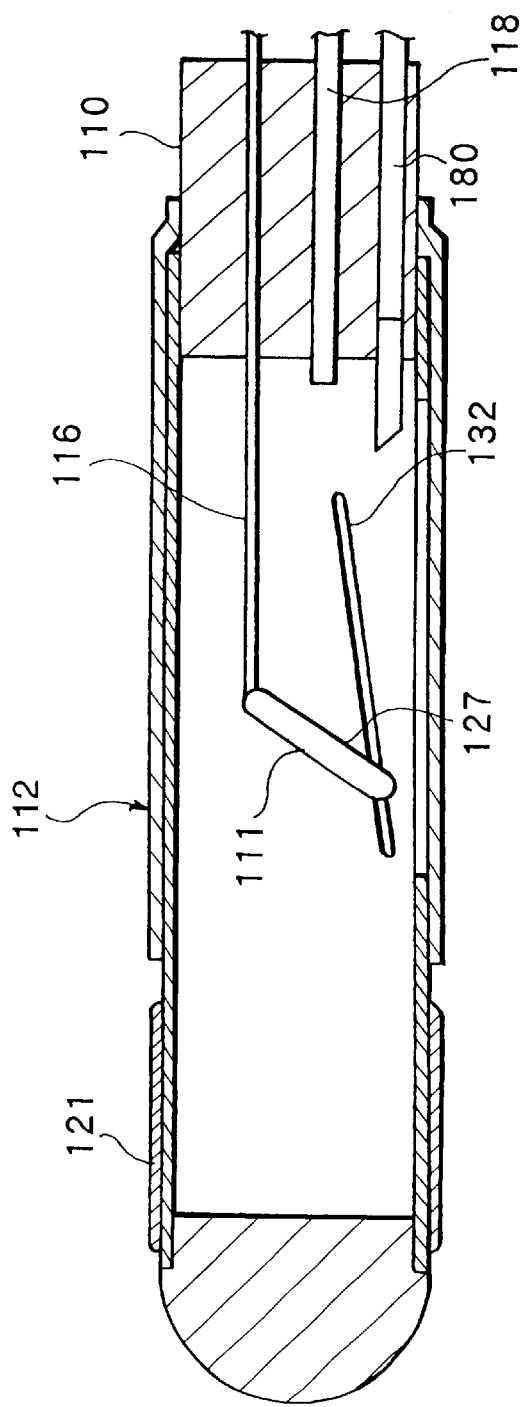
FIG. 29 is a sectional view of a housing for explaining an ultrasonic vibrator as a modification to the seventh embodiment.
Figure 30:
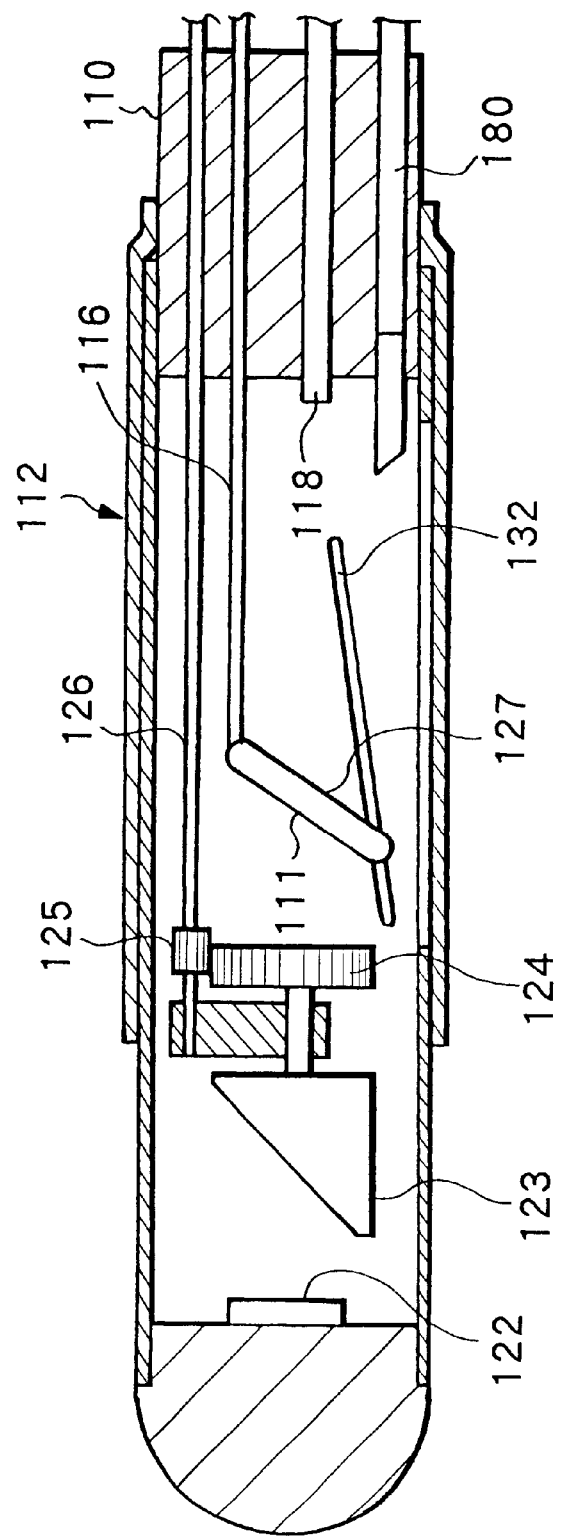
FIG. 30 is a sectional view of a housing for explaining an ultrasonic vibrator as another modification to the seventh embodiment.
Figure 31:
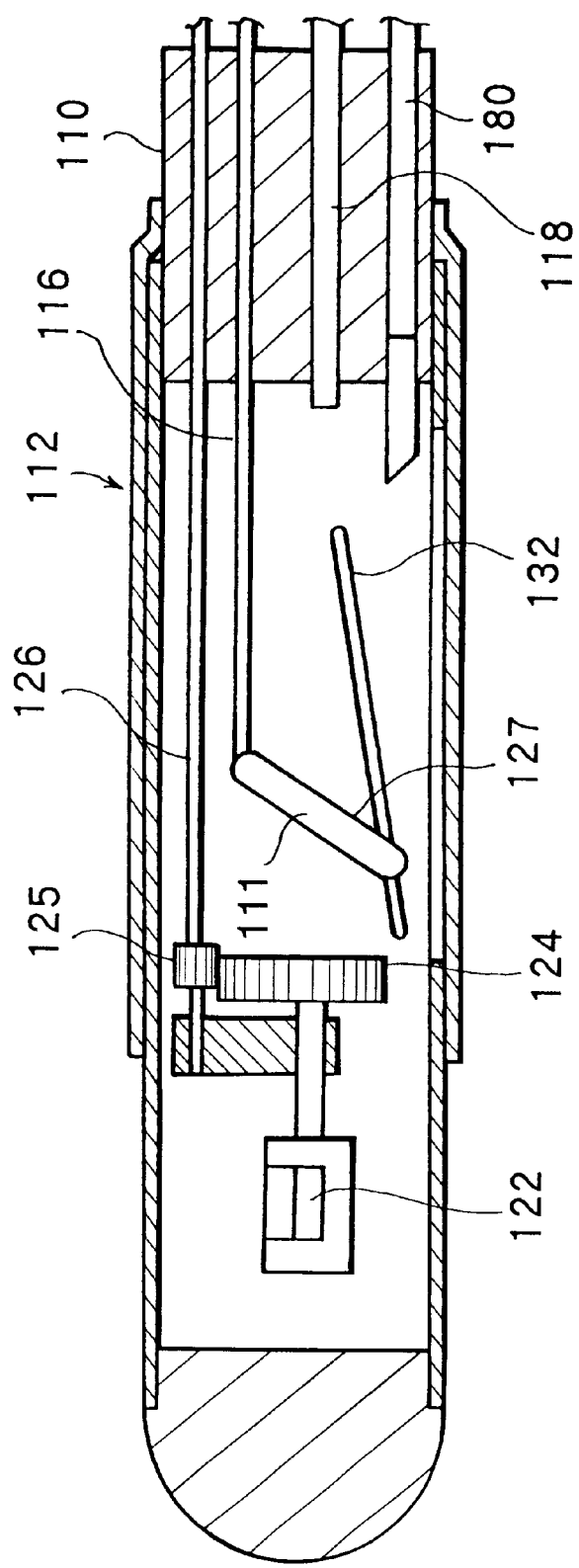
FIG. 31 is a sectional view of a housing for explaining an ultrasonic vibrator as still another modification to the seventh embodiment.

FIGS. 29 to 31 show modifications of this ultrasonic vibrator 121. In FIGS. 29 to 31, the same reference numerals as in the arrangement (FIG. 2) of the previously described embodiment denote the same parts, so a detailed description thereof will be omitted.

FIG. 29 is a sectional view showing an arrangement in which a plurality of ultrasonic vibrators 121 are arranged around the end portion of the housing 112. By electronically scanning these ultrasonic vibrators 121, ultrasonic scan can be performed in the entire circumferential direction of the housing 112.

FIG. 30 is a sectional view showing an arrangement in which an ultrasonic wave radiated from an ultrasonic vibrator 122 is reflected by a mirror 123 and radiated into a human body. This mirror 123 is rotated by rotating a rotating shaft 126 by a driving unit 150 and transmitting the rotation to the rotating shaft of the mirror 123 via gears 125 and 124. Consequently, ultrasonic scan can be performed in the whole circumferential direction of the housing 112.

FIG. 31 is a sectional view showing an arrangement in which an ultrasonic vibrator 122 is rotated to irradiate an ultrasonic wave in the whole circumferential direction of the housing 112. Also in this arrangement, the ultrasonic vibrator 122 is rotated by rotating a rotating shaft 126 by a driving unit 150 and transmitting the rotation to the rotating shaft of the ultrasonic vibrator 122 via gears 125 and 124. As a consequence, ultrasonic scan can be performed in the entire circumferential direction of the housing 112.

Figure 32:
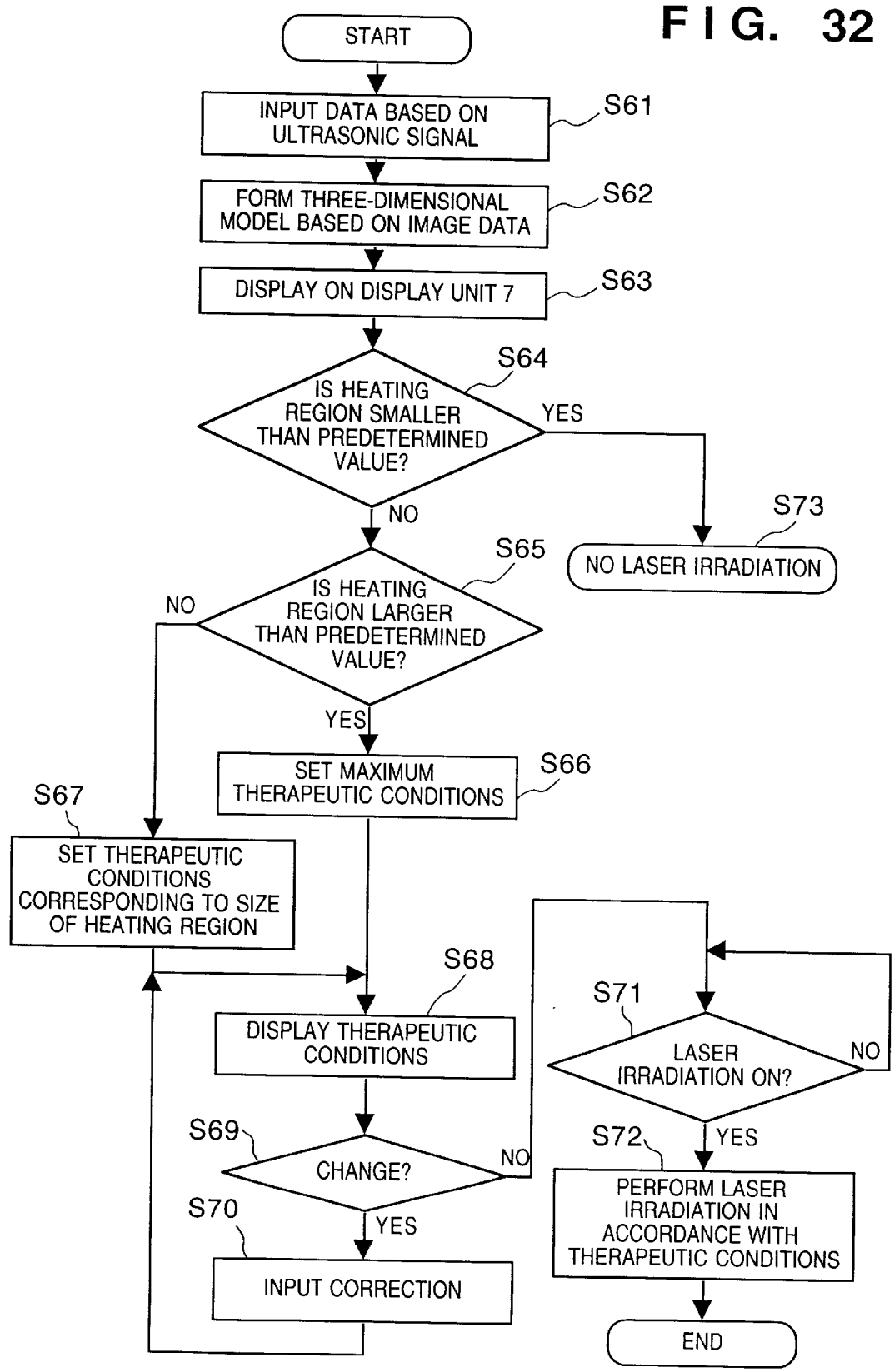
FIG. 32 is a flow chart for explaining a laser irradiation process using the medical laser irradiation apparatuses according to the fifth to seventh embodiments of the present invention.

FIG. 32 is a flow chart showing a laser irradiation process, based on an image sensing signal, performed by a controller 11 according to each of the above embodiments. Assume that an ultrasonic probe 14 is separated from a catheter 1 as shown in, e.g., FIG. 23.

In step S61, image data of a diseased part (e.g., a prostate) which is image-sensed on the basis of an ultrasonic signal from the ultrasonic probe 14 is input and analyzed by a signal analyzer 12. On the basis of the analytical result, a three-dimensional model (FIG. 26) of the diseased part is formed (step S62). This three-dimensional model is displayed on a display unit 7 (step S63). The signal analyzer 12 executes the procedure up to this point.

The flow then advances to step S64. In the case of thermal therapy of a prostate, for example, a urethra and its vicinity in the prostate, the perimeter and its vicinity of the prostate, and a portion along a vas deference are set as non-heating regions (not to be irradiated with a laser beam) in the shape of the diseased part, and the rest is set as a target heating region (to be irradiated with a laser beam). Whether the volume of this target heating region is smaller than a predetermined value is checked. If the volume is smaller than the predetermined value, in step S73 no laser irradiation to this target heating region is performed in order to prevent damage to the periphery of the prostate.

If the volume of the target heating portion is not smaller than the predetermined value in step S64, the flow advances to step S65 to check whether the volume of the target heating region is larger than a threshold value. If YES in step S65, the flow advances to step S66 to set laser beam irradiation conditions (to be described later) at maximum values. If NO in step S65, the flow advances to step S67, and therapeutic conditions based on experimental values or the like are set in accordance with the volume of the target heating region.

In step S68, the display unit 7 displays (step S68) the therapeutic conditions set in step S66 or S67. In step S69, whether designation to change the therapeutic conditions is input from an operation unit 8 is checked. If a change of the therapeutic conditions is designated and a correction value is input from the operation unit 8 in step S70, the display unit 7 displays the therapeutic conditions changed and corrected in accordance with the correction value.

If no change is designated in step S69 or if correction designation is completed, the operator inserts the catheter 1 into the urethra and positions a laser irradiating portion (window 115) to the prostate by using an endoscope 180.

Also, the operator resets the rotational angle of the catheter 1 measured by a potentiometer 191 to an initial value. The flow advances to step S71 to check whether a laser irradiation switch on the operation unit 8 is turned on. If the switch is turned on, the flow advances to step S72 to perform therapy by laser irradiation while the irradiation of a laser, the flow rate of a coolant, and the like are controlled in accordance with the currently set therapeutic conditions. As described previously, during the therapy a reflecting portion 111 in the housing 112 reflects the laser beam as it is moved back and forth in accordance with the therapeutic conditions. In this manner, the reflecting portion 111 irradiates the laser beam such that the laser beam concentrates on a desired position in a human body while preventing damage to the surface layer of the human body.

As a therapeutic condition not automatically set on the basis of analytical information of an image signal, a general therapeutic condition value in the thermal therapy is used. Note that a model formed in step S62 is not limited to a three-dimensional model but can be a two-dimensional model of a diseased part or a model including information which specifies the shape of a diseased part, e.g., the length, weight, volume, density, or blood flow rate of the diseased part.

In step S66 or S67, the heating conditions can also be set by using templates, as explained in the first to fourth embodiments described earlier.

FIG. 33 is a view for explaining parameter examples according to the seventh embodiment of the present invention.

The parameters include, e.g., the insentity (laser power) (unit: W) of a laser beam generated by the laser beam generator 2, the irradiation time (sec) of the laser beam, the flow rate (ml/min) of a coolant, and the moving velocity (round trips/sec) of the reflecting unit 111. In addition, the temperature of the coolant and the like can also be included.

To be able to analyze image diagnostic information obtained by an image diagnosing apparatus not included in the laser irradiation apparatus of this embodiment, an image input terminal can be installed in, e.g., the signal analyzer 12. Examples of the image diagnostic apparatus are apparatuses using an endoscope, an ultrasonic wave, MRI (Magnetic Resonance Imaging), CT (Computed Tomography) using X-rays or magnetic resonance, PET (Positron Emission Tomography), and SPECT (Single Photon Emission Computed Tomography).

The embodiments explained above are not described to limit the present invention but can be modified within the technical thought of the present invention. Also, in the above explanation the individual embodiments have been independently described. However, the present invention also includes any arbitrary combination of the arrangements of these embodiments. For example, it is possible to obtain the shape of a diseased part by using an ultrasonic probe in the fifth to seventh embodiments and arrange templates as described in the first embodiment on the basis of this shape. It is also possible to set heating regions by automatically arranging templates on the basis of the shape as in the third embodiment.

Additionally, energy to be irradiated toward a vital tissue has been described by taking a laser beam as an example. However, the present invention also includes a microwave, radio wave, ultrasonic wave, and the like.

Furthermore, a vital tissue to be thermally treated has been explained by taking a prostate as an example. However, the present invention includes all vital tissues, such as a blood vessel, a digestive tract (e.g., an esophagus and intestines), and an abdominal cavity, which can be thermally treated by irradiating energy from inside a human body or from the body surface.

The thermal therapy apparatus of the present invention is preferably applied to thermal therapy of a prostatic disease such as BPH; benign prostatic hyperplasia or a prostatic cancer, by which only the interior of a prostate is thermally treated while damage by heat to normal tissues such as a urethra and a rectum present near the prostate is reduced.

The present invention is not limited to the above embodiments and various changes and modifications can be made within the spirit and scope of the present invention. Therefore, to apprise the public of the scope of the present invention, the following claims are made.

What is claimed is:

1. A thermal therapy apparatus for treating a vital tissue by irradiating the tissue with energy, comprising:

energy generation means for generating energy;

a display configured to display a) a first cursor for designating a position of a cross section of a diseased part, b) a figure on a screen simulating the shape of a the cross section of the diseased part in accordance with the position designated by said first cursor, c) a plurality of preset identifiers, each preset identifier having a size defining an amount of heat energy to be irradiated by said energy generation means and having a shape defining a range for therapeutic treatment and d) a second cursor for selecting at least one of the preset identifiers;

an operating unit configured to operate the first cursor to designate the position of the cross section of the diseased part and move the second cursor to select a preset identifier among the plurality of preset identifiers displayed on the screen, and for allocating the selected preset identifier in the figure simulating the shape of the cross section of the diseased part on the screen of said display, so as to set the therapeutic conditions for the diseased part based on the size, shape and the arranged position of the preset identifier; and a controller configured to position said energy generation means in accordance with the position designated using the first cursor and control said energy generation means in accordance with the therapeutic conditions set by allocating the preset identifiers by said operating unit to treat the diseased part, wherein the diseased part is treated by the heat energy generated by said energy generation means in accordance with the therapeutic conditions.

2. The apparatus according to claim 1, wherein said operating unit arranges the heating region in accordance with a position designated in the figure indicating the shape of the diseased part and a predetermined conditional expression based on the position.

3. The apparatus according to claim 1 further comprising:

setting means for setting a non-heating region in the figure on the screen, wherein said controller controls therapeutic conditions of said thermal therapy apparatus in accordance with both size/position information of the heating region arranged by said operating unit and the non-heating region set by said setting means.

4. The apparatus according to claim 3, wherein said operating unit arranges the heating region in accordance with a position designated in the figure indicating the shape of the diseased part and a predetermined conditional expression based on the position.

5. The apparatus according to claim 3, further comprising:
transmitting means for transmitting the energy generated by said energy generation means into a catheter; and
energy concentrating means for concentrating the energy transmitted by said transmitting means on a desired portion in a human body by reflecting the energy while changing a position in said catheter.

6. The apparatus according to claim 3, wherein the therapeutic conditions include at least an energy intensity and an irradiation time.

7. The apparatus according to claim 3, wherein said therapeutic conditions include at least one of an energy intensity, an irradiation time, a velocity at which the position is changed in said catheter, and the flow rate and temperature of a coolant for cooling an energy irradiation.

8. The apparatus according to claim 3, wherein the energy is a laser beam.

9. The apparatus according to claim 1, further comprising:
an energy generator for generating the energy;
transmitting unit transmitting the energy generated by said energy generator into a catheter; and
energy concentrating unit concentrating the energy transmitted by said transmitting unit on a desired portion in a human body by reflecting the energy while changing a position in said catheter.

10. The apparatus according to claim 1, wherein the therapeutic conditions include at least an energy intensity and an irradiation time.

11. The apparatus according to claim 1, wherein said therapeutic conditions include at least one of an energy intensity, an irradiation time, a velocity at which the position is changed in said catheter, and the flow rate and temperature of a coolant for cooling an energy irradiation.

12. The apparatus according to claim 1, wherein the energy is a laser beam.

13. An apparatus according to claim 1, wherein the identifier designates at least a heating region and a heating direction of said energy generation means.

14. A thermal therapy apparatus comprising:
a catheter including heat energy irradiation means, to be inserted into a human body to irradiate a diseased part with heat energy;
designation means for designating a position of a cross section of a diseased part;
approximating means for approximating the shape of the cross section of the diseased part on the basis of shape data of the diseased part and the position of the cross section designated by said designation means;
setting means for setting a non-heating region in the shape approximated by said approximating means;
a display configure to display 1) a figure on a screen simulating the shape of the diseased part approximated by said approximating means, 2) preset identifiers, each defining a heating region and therapeutic conditions, and 3) the non-heating region set by said setting means and 4) a cursor for selecting the preset identifiers and allocating the selected identifiers;
allocating means for moving the cursor to select and allocate the selected preset identifiers, each having a shape and size defining a heating region and an amount of heat energy to be irradiated by the heat energy from said heat energy irradiation means, in the figure except for the non-heating region set by said setting means, wherein the selected preset identifiers are substantially uniformly arranged in the figure except for the non-heating region; and a controller configured to control the heat energy to irradiate a diseased part in accordance with the therapeutic conditions in correspondence to the selected identifiers and the allocated positions of the preset identifiers.

15. The apparatus according to claim 14, wherein said allocating means selects an identifier from a plurality of pre-stored identifiers, and arranges a selected identifier in the figure on the screen so as to arrange the heating region in the target heating region.

16. The apparatus according to claim 14, further comprising:
determining means for determining control information of said energy irradiation means on the basis of the heating regions allocated by said allocating means; and
the controller controlling said energy irradiation means in accordance with the control information determined by said determining means.

17. The apparatus according to claim 16, wherein the control information includes at least information concerning an irradiation angle and the number of times of irradiation of the energy.

18. The apparatus according to claim 16, further comprising rotational angle control unit controlling a view angle of the catheter in accordance with the control information.

19. The apparatus according to claim 16, further comprising selecting means for selecting one of automatic heating and manual heating of the diseased part in accordance with the control information determined by said determining means.

20. The apparatus according to claim 14, wherein said energy irradiation means comprises:
an energy generator for generating the energy;
transmitting unit transmitting the energy generated by said energy generator into the catheter; and
energy concentrating unit concentrating the energy transmitted by said transmitting means on a desired portion in a human body by reflecting the energy while changing a position in said catheter.

21. The apparatus according to claim 14, wherein the energy is a laser beam.

22. An apparatus according to claim 14, wherein the identifier designates at least a heating region and a heating direction of said energy irradiation means.

23. A medical heating apparatus for performing thermal therapy by irradiating a vital tissue with energy, comprising:
energy generation means for generating heat energy;
image acquiring means for acquiring an image signal of a diseased part as an object of the thermal therapy;
signal analyzing means for analyzing the image signal acquired by said image acquiring means;
designation means for designating a position of a cross section of the diseased part;
setting means for setting therapeutic conditions for performing the thermal therapy on the basis of analytical information obtained by said signal analyzing means;
a display configured to display a) a figure simulating the shape of the cross section of the diseased part, b) a plurality of preset identifiers, each preset identifier having a size defining an amount of energy to be irradiated by the heat energy from said energy generation means and a shape defining a range for therapeutic treatment and c) a cursor for selecting at least one of the preset identifiers;
an operating unit configured to move the cursor to select an identifier from a plurality of identifiers displayed on the screen of the display, and allocate a selected identifier in the figure simulating the shape of the cross section to designate the therapeutic conditions for the diseased part, based on the size, shape and the allocated position of the preset identifiers; and a controller configured to control irradiation of the diseased part with the heat energy according to the therapeutic conditions in correspondence to the selected identifier and the allocated position of the preset identifier.

24. The apparatus according to claim 23, wherein the analytical information includes information for specifying the shape of the diseased part.

25. The apparatus according to claim 23, wherein said unit energy generation means comprises a long insertion portion which can be inserted into a human body and irradiates the diseased part with energy from an irradiation portion installed in said insertion portion.

26. The apparatus according to claim 25, wherein said insertion portion contains said image acquiring means.

27. The apparatus according to claim 25, wherein said insertion portion has a lumen into which said image acquiring means can be inserted.

28. The apparatus according to claim 25, further comprising cooling unit cooling said irradiation portion and an energy irradiation surface and its vicinity of the vital tissue.

29. The apparatus according to claim 25, further comprising:

moving unit moving the position of said irradiation portion in a longitudinal direction of said insertion portion; and interlocking unit changing the irradiation angle of energy irradiating the diseased part in accordance with the movement in the longitudinal direction of said insertion portion.

30. The apparatus according to claim 23, wherein said image acquiring unit acquires an image signal on the basis of an ultrasonic wave transmitted and received by an ultrasonic vibrator.

31. The apparatus according to claim 23, wherein said energy generation means performs irradiation of a laser beam as energy.

32. The apparatus according to claim 23, wherein the therapeutic conditions include not less than one item selected from the group consisting of the number of times of irradiation of the energy, the irradiation direction of the energy, the intensity of the energy, the irradiation time of the energy, the temperature of a coolant when the coolant is used, the flow rate of the coolant when the coolant is supplied, and the moving velocity of said energy generation means for performing irradiation of energy when said energy generation means is moved.

33. The apparatus according to claim 23, further comprising means for inhibiting the thermal therapy when the analytical information is smaller than a preset minimum value.

34. The apparatus according to claim 23, further comprising means for setting preset maximum therapeutic conditions as therapeutic conditions when the analytical information indicates that the diseased part is larger than a preset maximum value.

35. The apparatus according to claim 23, wherein said controller for performing the thermal therapy by controlling, in accordance with the therapeutic conditions set by said setting means, said energy generation means and at least one item selected from the group consisting of the number of irradiation times of the energy, the irradiation direction of the energy, the intensity of the energy, the irradiation time of the energy, the temperature of a coolant when the coolant is used, the flow rate of the coolant when the coolant is supplied, and the moving velocity of said energy generation means for performing irradiation of energy when said energy generation means is moved.

36. The apparatus according to claim 29, wherein said operating unit arranges the heating region in accordance with a position designated in the figure indicating the shape of the diseased part and a predetermined conditional expression based on the position.

37. The apparatus according to claim 23, further comprising:

approximating means for approximating the shape of the diseased part on the basis of the image signal;

non-heating setting means for setting a non-heating region in the shape approximated by said approximating means;

allocating means for substantially uniformly allocating heating regions, to be heated, in a target heating region except for the non-heating region; and the display displaying a figure indicating a shape of the diseased part approximated by said approximating means, the heating regions allocated by said allocating means, and the non-heating region set by said non-heating setting means.

38. The apparatus according to claim 37, wherein said allocating means selects an identifier from a plurality of identifiers that are stored in advance, and arranges the heating region by arranging the selected identifier in the figure.

39. The apparatus according to claim 37, further comprising:

determining means for determining control information of said energy generation means on the basis of the heating regions allocated by said allocating means; and the controller controlling said energy generation means in accordance with the control information determined by said determining means.

40. The apparatus according to claim 39, wherein the control information includes at least information concerning an irradiation angle and the number of times of irradiation of the energy.

41. The apparatus according to claim 39, further comprising rotational angle control means for controlling a view angle of a catheter in accordance with the control information.

42. The apparatus according to claim 39, further comprising selecting means for selecting one of automatic heating and manual heating of the diseased part in accordance with the control information determined by said determining means.

43. The apparatus according to claim 23, wherein said energy generation means comprises:

an energy generator generating the heat energy;

transmitting unit transmitting the energy generated by said energy generator into a catheter; and energy concentrating unit for concentrating the energy transmitted by said transmitting unit on a desired portion in a human body by reflecting the energy while changing a position in said catheter.

44. An apparatus according to claim 23, wherein the identifier designates at least a heating region and a heating direction of said energy generation means.

* * * * *

UNITED STATES PATENT AND TRADEMARK OFFICE
CERTIFICATE OF CORRECTION

PATENT NO.     : 6,695,871 B1
DATED          : February 24, 2004
INVENTOR(S)    : Shin Maki et al.

It is certified that error appears in the above-identified patent and that said Letters Patent is hereby corrected as shown below:

Title page,
Item [*] Notice, delete the statement "This patent issued on a continued prosecution application filed under 37 CFR 1.53(d), and is subject to the twenty year patent term provisions of 35 U.S.C. 154 (a)(2)."

Signed and Sealed this

Eighteenth Day of October, 2005

JON W. DUDAS
*Director of the United States Patent and Trademark Office*